United States Patent
Rao et al.

(10) Patent No.: US 9,540,540 B2
(45) Date of Patent: *Jan. 10, 2017

(54) SULFONE-CONTAINING POLYTHIOETHERS, COMPOSITIONS THEREOF, AND METHODS OF SYNTHESIS

(71) Applicant: PRC-DeSoto International, Inc., Sylmar, CA (US)

(72) Inventors: Chandra Rao, Valencia, CA (US); Juexiao Cai, Stevenson Ranch, CA (US); Renhe Lin, Stevenson Ranch, CA (US)

(73) Assignee: PRC-DeSoto International, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/708,314

(22) Filed: May 11, 2015

(65) Prior Publication Data

US 2015/0240122 A1 Aug. 27, 2015

Related U.S. Application Data

(63) Continuation of application No. 13/833,827, filed on Mar. 15, 2013, now Pat. No. 9,062,139.

(51) Int. Cl.

| | | |
|---|---|---|
| C09D 181/02 | (2006.01) |
| C08F 228/04 | (2006.01) |
| C07C 317/18 | (2006.01) |
| C08G 75/20 | (2016.01) |
| C08G 75/23 | (2006.01) |
| C08G 75/00 | (2006.01) |
| C08G 75/02 | (2016.01) |
| C08L 81/00 | (2006.01) |
| C08L 81/02 | (2006.01) |
| C08L 81/04 | (2006.01) |
| C07C 317/04 | (2006.01) |

(52) U.S. Cl.
CPC ........... *C09D 181/02* (2013.01); *C07C 317/04* (2013.01); *C07C 317/18* (2013.01); *C08F 228/04* (2013.01); *C08G 75/00* (2013.01); *C08G 75/02* (2013.01); *C08G 75/20* (2013.01); *C08G 75/23* (2013.01); *C08L 81/00* (2013.01); *C08L 81/02* (2013.01); *C08L 81/04* (2013.01)

(58) Field of Classification Search
None
See application file for complete search history.

(56) References Cited

U.S. PATENT DOCUMENTS

| | | | |
|---|---|---|---|
| 2,505,366 A * | 4/1950 | Schoene | C08G 65/002 528/375 |
| 3,215,677 A | 11/1965 | Le Fave et al. | |
| 3,386,958 A | 6/1968 | Remes et al. | |
| 4,059,570 A | 11/1977 | Oswald | |
| 4,366,307 A | 12/1982 | Singh et al. | |
| 4,609,762 A | 9/1986 | Morris et al. | |
| 5,225,472 A | 7/1993 | Cameron et al. | |
| 5,270,364 A | 12/1993 | Schwartz et al. | |
| 5,284,888 A | 2/1994 | Morgan | |
| 5,959,071 A * | 9/1999 | DeMoss | C08G 75/045 524/186 |
| 6,172,179 B1 | 1/2001 | Zook et al. | |
| 6,184,280 B1 | 2/2001 | Shibuta | |
| 6,509,418 B1 | 1/2003 | Zook et al. | |
| 6,525,168 B2 | 2/2003 | Zook et al. | |
| 7,009,032 B2 | 3/2006 | Bojkova et al. | |
| 7,563,859 B2 * | 7/2009 | Galbiati | C08G 75/0277 528/30 |
| 7,671,145 B2 | 3/2010 | Sawant et al. | |
| 8,541,513 B2 | 9/2013 | Hobbs et al. | |
| 2004/0247792 A1 | 12/2004 | Sawant et al. | |
| 2010/0010133 A1 | 1/2010 | Zook et al. | |
| 2010/0041839 A1 | 2/2010 | Anderson et al. | |
| 2011/0319559 A1 | 12/2011 | Kania et al. | |
| 2012/0234205 A1 | 9/2012 | Hobbs et al. | |
| 2012/0238708 A1 | 9/2012 | Hobbs et al. | |
| 2013/0345371 A1 | 12/2013 | Anderson et al. | |

FOREIGN PATENT DOCUMENTS

| | | |
|---|---|---|
| WO | 99/20668 A1 | 4/1999 |
| WO | WO 99/20668 * | 4/1999 |
| WO | 2013/192279 A2 | 12/2013 |
| WO | 2013/192297 A2 | 12/2013 |
| WO | 2013/192480 A2 | 12/2013 |
| WO | 2014/150463 A1 | 9/2014 |

OTHER PUBLICATIONS

International Search Report for Application No. PCT/US2014/023325, mailed on Aug. 13, 2014, 4 pages.
Non-Final Office Action for U.S. Appl. No. 13/833,827, mailed on Oct. 31, 2014, 7 pages.
Notice of Allowance for U.S. Appl. No. 13/833,827, mailed on Feb. 12, 2015, 8 pages.

* cited by examiner

*Primary Examiner* — Robert C Boyle
(74) *Attorney, Agent, or Firm* — William R. Lambert

(57) ABSTRACT

Sulfone-containing polythioethers, compositions containing sulfone-containing polythioethers, methods of synthesizing sulfone-containing polythioethers and the use of sulfone-containing polythioethers in aerospace sealant applications are disclosed. The sulfone-containing polythioethers have sulfone groups incorporated into the backbone of the polythioether. Cured sealant compositions comprising the sulfone-containing polythioethers exhibit enhanced thermal resistance.

20 Claims, No Drawings

SULFONE-CONTAINING POLYTHIOETHERS, COMPOSITIONS THEREOF, AND METHODS OF SYNTHESIS

This application is a continuation of U.S. application Ser. No. 13/833,827, filed on Mar. 15, 2013, which is incorporated by reference in its entirety.

FIELD

The present disclosure relates to sulfone-containing polythioethers, compositions containing sulfone-containing polythioethers, methods of synthesizing sulfone-containing polythioethers and uses of sulfone-containing polythioethers in aerospace sealant applications. The sulfone-containing polythioethers contain sulfone groups incorporated into the backbone of the polythioether.

BACKGROUND

Sealants useful in aerospace and other applications must satisfy demanding mechanical, chemical, and environmental requirements. For example, it is desirable that aerospace sealants function over at temperature range such as from about −67° F. to about 360° F. Michael addition curing chemistries employing divinyl sulfone and sulfur-containing polymers have been shown to produce aerospace sealants having faster cure rates and enhanced performance including fuel resistance and thermal resistance. For example, in the systems disclosed in U.S. application Ser. No. 13/529,237, filed on Jun. 21, 2012, sulfur-containing polymer adducts such as polythioether adducts containing terminal Michael acceptor groups such as vinyl sulfone groups are reacted with a curing agent such as a thiol-terminated sulfur-containing polymer to form a cured composition. Application of Michael addition curing chemistries to sulfur-containing polymers not only results in cured sealants with faster cure rates and enhanced performance including fuel resistance and thermal resistance, but also provides a sealant with improved physical properties such as elongation.

SUMMARY

In a first aspect, sulfone-containing polythioethers are provided comprising a moiety of Formula (1):

$$\text{-A-CH}_2\text{—CH}_2\text{—S(O)}_2\text{—CH}_2\text{—CH}_2\text{-A-} \quad (1)$$

wherein each A is independently a moiety of Formula (2):

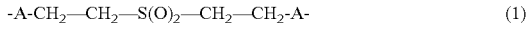

(2)

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $\text{—}[(\text{—CHR}^3\text{—})_s\text{—X—}]_q\text{—}(\text{—CHR}^3\text{—})_r\text{—}$, wherein:
s is an integer from 2 to 6;
q is an integer from 1 to 5;
r is an integer from 2 to 10;
each $R^3$ independently comprises hydrogen or methyl; and
each X independently comprises —O—, —S—, or —NR$^5$—, wherein R$^5$ comprises hydrogen or methyl; and
each $R^2$ independently comprises $C_{1-10}$ alkanediyl, $C_{6-8}$ cycloalkanediyl, $C_{6-14}$ alkanecycloalkanediyl, or $\text{—}[(\text{—CHR}^3\text{—})_s\text{—X—}]_q\text{—}(\text{—CHR}^3\text{—})_r\text{—}$, wherein s, q, r, $R^3$, and X are as defined for $R^1$;

m is an integer from 0 to 50;
n is an integer from 1 to 60; and
p is an integer from 2 to 6.

In a second aspect, thiol-terminated sulfone-containing polythioethers are provided comprising the reaction product of reactants comprising:

(a) a thiol-terminated polythioether adduct comprising a thiol-terminated adduct of Formula (4), a thiol-terminated adduct of Formula (4a), or a combination thereof:

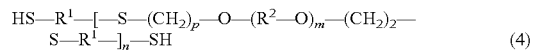

(4)

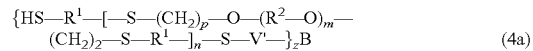

(4a)

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $\text{—}[(\text{—CHR}^3\text{—})_s\text{—X—}]_q\text{—}(\text{—CHR}^3\text{—})_r\text{—}$, wherein:
s is an integer from 2 to 6;
q is an integer from 1 to 5;
r is an integer from 2 to 10;
each $R^3$ independently comprises hydrogen or methyl; and
each X independently comprises —O—, —S—, or —NR$^5$—, wherein R$^5$ is selected from hydrogen and methyl;
each $R^2$ independently comprises $C_{1-10}$ alkanediyl, $C_{6-8}$ cycloalkanediyl, $C_{6-14}$ alkanecycloalkanediyl, or $\text{—}[(\text{—CHR}^3\text{—})_s\text{—X—}]_q\text{—}(\text{—CHR}^3\text{—})_r\text{—}$,
wherein s, q, r, $R^3$, and X are as defined for $R^1$;
m is an integer from 0 to 50;
n is an integer from 1 to 60;
p is an integer from 2 to 6; and
B represents a core of a z-valent, alkenyl-terminated polyfunctionalizing agent B(—V)$_z$ wherein:
z is an integer from 3 to 6; and
each V is a group comprising a terminal alkenyl group; and
each —V'— is derived from the reaction of —V with a thiol; and (b) a sulfone of Formula (5):

(5).

In a third aspect, thiol-terminated sulfone-containing polythioether prepolymers are provided comprising the reaction product of reactants comprising:

(a) a thiol-terminated sulfone-containing adduct comprising thiol-terminated sulfone-containing adduct of Formula (6), thiol-terminated sulfone-containing adduct of Formula (6a), or a combination thereof:

$$\text{H-A-[—CH}_2\text{—CH}_2\text{—S(O)}_2\text{—CH}_2\text{—CH}_2\text{-A-]}_N\text{—H} \quad (6)$$

$$\{\text{H-A-CH}_2\text{—CH}_2\text{—S(O)}_2\text{—CH}_2\text{—CH}_2\text{-A-V'—}\}_z\text{B} \quad (6a)$$

wherein
N is an integer from 1 to 10;
each A is independently a moiety of Formula (2):

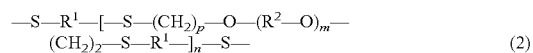

(2)

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or $\text{—}[(\text{—CHR}^3\text{—})_s\text{—X—}]_q\text{—}(\text{—CHR}^3\text{—})_r\text{—}$, wherein:
s is an integer from 2 to 6;
q is an integer from 1 to 5;
r is an integer from 2 to 10;
each $R^3$ independently comprises hydrogen or methyl; and
each X independently comprises —O—, —S—, or —$NR^5$—, wherein $R^5$ comprises hydrogen or methyl;
each $R^2$ independently comprises $C_{1-10}$ alkanediyl, $C_{6-8}$ cycloalkanediyl, $C_{6-14}$ alkanecycloalkanediyl, or —[($CHR^3$—)$_s$—X—]$_q$—($CHR^3$—)$_r$—, wherein s, q, r, $R^3$, and X are as defined for $R^1$;
m is an integer from 0 to 50;
n is an integer from 1 to 60; and
p is an integer from 2 to 6;
B represents a core of a z-valent, alkenyl-terminated polyfunctionalizing agent B(—V)$_z$ wherein:
z is an integer from 3 to 6;
each V is a group comprising a terminal alkenyl group; and each —V'— is derived from the reaction of —V with a thiol; and
(b) a polyalkenyl compound.

In a fourth aspect, methods of preparing a thiol-terminated sulfone-containing polythioether adduct of Formula (6) are provided, comprising reacting (N+1) moles of a thiol-terminated polythioether of Formula (4) with (N) moles of a sulfone of Formula (5):

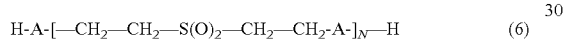

$$H\text{-}A\text{-}[-CH_2-CH_2-S(O)_2-CH_2-CH_2\text{-}A\text{-}]_N-H \quad (6)$$

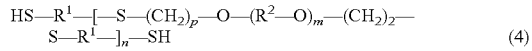

$$HS-R^1-[-S-(CH_2)_p-O-(R^2-O)_m-(CH_2)_2-S-R^1-]_n-SH \quad (4)$$

$$CH_2=CH-S(O)_2-CH=CH_2 \quad (5)$$

wherein:
N is an integer from 1 to 10;
each A is independently a moiety of Formula (2):

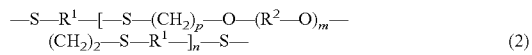

$$-S-R^1-[-S-(CH_2)_p-O-(R^2-O)_m-(CH_2)_2-S-R^1-]_n-S- \quad (2)$$

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—$CHR^3$—)$_s$—X—]$_q$—(—$CHR^3$—)$_r$—, wherein:
s is an integer from 2 to 6;
q is an integer from 1 to 5;
r is an integer from 2 to 10;
each $R^3$ independently comprises hydrogen or methyl; and
each X independently comprises —O—, —S—, or —$NR^5$—, wherein $R^5$ comprises hydrogen or methyl; and
each $R^2$ is independently comprises $C_{1-10}$ alkanediyl, $C_{6-8}$ cycloalkanediyl, $C_{6-14}$ alkanecycloalkanediyl, or —[(—$CHR^3$—)$_s$—X—]$_q$—(—$CHR^3$—)$_r$—, wherein s, q, r, $R^3$, and X are as defined for $R^1$;
m is an integer from 0 to 50;
n is an integer from 1 to 60;
p is an integer from 2 to 6.

In a fifth aspect, methods of preparing a thiol terminated sulfone-containing polythioether adduct of Formula (6a) are provided comprising reacting (z) moles of a thiol-terminated sulfone-containing polythioether adduct of Formula (6) with one (1) mole of a polyfunctionalizing agent of Formula (7):

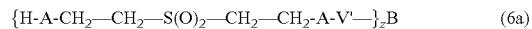

$$\{H\text{-}A\text{-}CH_2-CH_2-S(O)_2-CH_2-CH_2\text{-}A\text{-}V'-\}_zB \quad (6a)$$

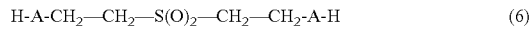

$$H\text{-}A\text{-}CH_2-CH_2-S(O)_2-CH_2-CH_2\text{-}A\text{-}H \quad (6)$$

$$B\{V\}_z \quad (7)$$

wherein:
each A is independently a moiety of Formula (2):

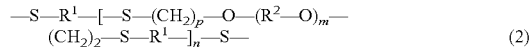

$$-S-R^1-[-S-(CH_2)_p-O-(R^2-O)_m-(CH_2)_2-S-R^1-]_n-S- \quad (2)$$

wherein:
each $R^1$ independently comprises $C_{2-10}$ alkanediyl, $C_{6-8}$ cycloalkanediyl, $C_{6-10}$ alkanecycloalkanediyl, $C_{5-8}$ heterocycloalkanediyl, or —[(—$CHR^3$—)$_s$—X—]$_q$—(—$CHR^3$—)$_r$—,
wherein:
s is an integer from 2 to 6;
q is an integer from 1 to 5;
r is an integer from 2 to 10;
each $R^3$ independently comprises hydrogen or methyl; and
each X independently comprises —O—, —S—, and —$NR^5$—, wherein $R^5$ comprises hydrogen or methyl;
each $R^2$ is independently selected from $C_{1-10}$ alkanediyl, $C_{6-8}$ cycloalkanediyl, $C_{6-14}$ alkanecycloalkanediyl, or —[(—$CHR^3$—)$_s$—X—]$_q$—(—$CHR^3$—)$_r$—, wherein s, q, r, $R^3$, and X are as defined for $R^1$;
m is an integer from 0 to 50;
n is an integer from 1 to 60; and
p is an integer from 2 to 6;
B represents a core of a z-valent, alkenyl-terminated polyfunctionalizing agent B(—V)$_z$ wherein:
z is an integer from 3 to 6;
each V is a group comprising a terminal alkenyl group; and
each —V'— is derived from the reaction of —V with a thiol.

In a sixth aspect, compositions are provided comprising (a) a sulfone-containing polythioether provided by the present disclosure; and (b) a curing agent that is reactive with the terminal groups of the sulfone-containing polythioether.

In a seventh aspect, cured sealants formed from a composition comprising a sulfone-containing polythioether provided by the present disclosure are provided.

In an eighth aspect, apertures sealed with a composition comprising a sulfone-containing polythioether provided by present disclosure are provided.

In a ninth aspect, methods of sealing an aperture are provided comprising (a) applying a composition comprising a sulfone-containing polythioether provided by the present disclosure formulated as a sealant to at least one surface defining an aperture; (b) assembling the surfaces defining the aperture; and (c) curing the applied composition to provide a sealed aperture.

DETAILED DESCRIPTION

Definitions

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of about 1 and the recited maximum value of about 10, that is, having a minimum value equal to or greater than about 1 and a maximum value of equal to or less than about 10. Also, in this application, the use of "or" means "and/or" unless specifically stated otherwise, even though "and/or" may be explicitly used in certain instances.

A dash ("-") that is not between two letters or symbols is used to indicate a point of bonding for a substituent or between two atoms. For example, —CONH$_2$ is bonded to another chemical moiety through the carbon atom.

"Alkanediyl" refers to a diradical of a saturated, branched or straight-chain, acyclic hydrocarbon group, having, for example, from 1 to 18 carbon atoms ($C_{1-18}$), from 1 to 14 carbon atoms ($C_{1-14}$), from 1 to 6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. In certain embodiments, the alkanediyl is $C_{2-14}$ alkanediyl, $C_{2-10}$ alkanediyl, $C_{2-8}$ alkanediyl, $C_{2-6}$ alkanediyl, $C_{2-4}$ alkanediyl, and in certain embodiments, $C_{2-3}$ alkanediyl. Examples of alkanediyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, decane-1,10-diyl, dodecane-1,12-diyl, and the like.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. In certain embodiments, each cycloalkyl and/or cycloalkanediyl group(s) is $C_{3-6}$, $C_{5-6}$, and in certain embodiments, cyclohexyl or cyclohexanediyl. In certain embodiments, each alkyl and/or alkanediyl group(s) is $C_{1-6}$, $C_{1-4}$, $C_{1-3}$, and in certain embodiments, methyl, methanediyl, ethyl, or ethane-1,2-diyl. In certain embodiments, the alkanecycloalkane group is $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, and in certain embodiments, $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. In certain embodiments, the alkanecycloalkanediyl group is $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, and in certain embodiments, $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkenyl" group refers to a group (R)$_2$C=C(R)$_2$. In certain embodiments, an alkenyl group has the structure —CR=CR$_2$ where the alkenyl group is a terminal group and is bonded to a larger molecule. In such embodiments, each R may be selected from, for example, hydrogen and $C_{1-3}$ alkyl. In certain embodiments, each R is hydrogen and an alkenyl group has the structure —CH=CH$_2$.

"Alkoxy" refers to a —OR group where R is alkyl as defined herein. Examples of alkoxy groups include methoxy, ethoxy, n-propoxy, isopropoxy, and n-butoxy. In certain embodiments, the alkoxy group is $C_{1-8}$ alkoxy, $C_{1-6}$ alkoxy, $C_{1-4}$ alkoxy, and in certain embodiments, $C_{1-3}$ alkoxy.

"Alkyl" refers to a monoradical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. In certain embodiments, the alkyl group is $C_{2-6}$ alkyl, $C_{24}$ alkyl, and in certain embodiments, $C_2$-3 alkyl. Examples of alkyl groups include methyl, ethyl, n-propyl, iso-propyl, n-butyl, iso-butyl, tert-butyl, n-hexyl, n-decyl, tetradecyl, and the like. In certain embodiments, the alkyl group is $C_{2-6}$ alkyl, $C_2$-4 alkyl, and in certain embodiments, $C_2$-3 alkyl. It will be appreciated that a branched alkyl has at least three carbon atoms.

"Cycloalkanediyl" refers to a diradical saturated monocyclic or polycyclic hydrocarbon group. In certain embodiments, the cycloalkanediyl group is $C_{3-12}$ cycloalkanediyl, $C_{3-8}$ cycloalkanediyl, $C_{3-6}$ cycloalkanediyl, and in certain embodiments, $C_{5-6}$ cycloalkanediyl. Examples of cycloalkanediyl groups include cyclohexane-1,4-diyl, cyclohexane-1,3-diyl, and cyclohexane-1,2-diyl.

"Cycloalkyl" refers to a saturated monocyclic or polycyclic hydrocarbon monoradical group. In certain embodiments, the cycloalkyl group is $C_{3-12}$ cycloalkyl, $C_{3-8}$ cycloalkyl, $C_{3-6}$ cycloalkyl, and in certain embodiments, $C_{5-6}$ cycloalkyl.

"Heterocycloalkanediyl" refers to a cycloalkanediyl group in which one or more of the carbon atoms are replaced with a heteroatom, such as N, O, S, or P. In certain embodiments of heterocycloalkanediyl, the heteroatom is selected from N and O.

As used herein, "polymer" refers to oligomers, homopolymers, and copolymers. Unless stated otherwise, molecular weights are number average molecular weights for polymeric materials indicated as "$M_n$" as determined, for example, by gel permeation chromatography using a polystyrene standard in an art-recognized manner.

Reference is now made to certain embodiments of sulfone-containing polythioethers compositions thereof, and methods of synthesis. The disclosed embodiments are not intended to be limiting of the claims. To the contrary, the claims are intended to cover all alternatives, modifications, and equivalents.

To enhance the thermal resistance of cured aerospace sealants, sulfones are incorporated into the backbone of sulfur-containing prepolymers. The sulfone-containing sulfur-containing prepolymers can be adapted for any suitable curing chemistry. For example, thiol-terminated sulfone-containing polythioether prepolymers and polyepoxy curing agents provide sealants useful for aerospace applications.

Sulfone-containing Polythioethers

Sulfone-containing polythioethers provided by the present disclosure are characterized by having one or more sulfone groups incorporated into the backbone of the polythioether.

Polythioethers useful in aerospace sealant applications are disclosed, for example, in U.S. Pat. No. 6,172,179. Polythioethers refer to compounds comprising at least two thioether, —C—S—C— linkages. Polythioethers may be prepared, for example, by reacting dithiols with divinyl ethers. In general, thiol-terminated sulfone-containing polythioethers may be prepared by reacting divinyl sulfone with one or more dithols or polythiol to prepare a thiol-terminated sulfone-containing polythioether adduct.

In certain embodiments, sulfone-containing polythioethers comprise a backbone comprising the structure of Formula (1):

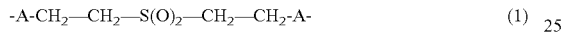

-A-CH$_2$—CH$_2$—S(O)$_2$—CH$_2$—CH$_2$-A-     (1)

wherein each A is independently a moiety of Formula (2):

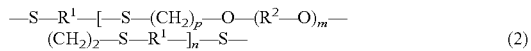

—S—R$^1$—[—S—(CH$_2$)$_p$—O—(R$^2$—O)$_m$—(CH$_2$)$_2$—S—R$^1$—]$_n$—S—     (2)

wherein:
  each R$^1$ is independently selected from C$_{2-10}$ alkanediyl, C$_{6-8}$ cycloalkanediyl, C$_{6-10}$ alkanecycloalkanediyl, C$_{5-8}$ heterocycloalkanediyl, and —[(—CHR$^3$—)$_s$—X—]$_q$—(CHR$^3$—)$_r$—, wherein:
    s is an integer from 2 to 6;
    q is an integer from 1 to 5;
    r is an integer from 2 to 10;
    each R$^3$ is independently selected from hydrogen and methyl; and
    each X is independently selected from —O—, —S—, and —NR$^5$—, wherein R$^5$ is selected from hydrogen and methyl; and
  each R$^2$ is independently selected from C$_{1-10}$ alkanediyl, C$_{6-8}$ cycloalkanediyl, C$_{6-14}$ alkanecycloalkanediyl, and —[(—CHR$^3$—)$_s$—X—]$_q$—(CHR$^3$—)$_r$—, wherein s, q, r, R$^3$, and X are as defined for R$^1$;
  m is an integer from 0 to 50;
  n is an integer from 1 to 60; and
  p is an integer from 2 to 6.

In certain embodiments of Formula (1) and Formula (2), each R$^1$ is —[—(CHR$^3$)$_s$—X-]$_q$—(CHR$^3$)$_r$— wherein each X is independently selected from —O— and —S—. In certain embodiments wherein R$^1$ is —[—(CHR$^3$)$_s$—X—]$_q$—(CHR$^3$)—, each X is —O— and in certain embodiments, each X is —S—. In certain embodiments, each R$^3$ is hydrogen.

In certain embodiments of Formula (1) and Formula (2), each R$^1$ is —[—(CH$_2$)$_s$—X-]$_q$—(CH$_2$)$_r$— wherein each X is independently selected from —O— and —S—. In certain embodiments wherein R$^1$ is —[—(CH$_2$)$_s$—X—]—(CH$_2$)$_r$—, each X is —O— and in certain embodiments, each X is —S—.

In certain embodiments of Formula (1) and Formula (2), each R$^1$ in Formula (2) is —[(—CH$_2$—)$_s$—X—]—(CH$_2$)$_r$—, where s is 2, X is O, q is 2, r is 2, R$^2$ is ethanediyl, m is 2, and n is 9.

In certain embodiments of Formula (1) and Formula (2), each R$^1$ is derived from dimercaptodioxaoctane (DMDO) and in certain embodiments, each R$^1$ is derived from dimercaptodiethylsulfide (DMDS).

In certain embodiments of Formula (1) and Formula (2), each m is independently an integer from 1 to 3. In certain embodiments, each m is the same and is 1, 2, and in certain embodiments, 3.

In certain embodiments of Formula (1) and Formula (2), n is an integer from 1 to 30, an integer from 1 to 20, an integer from 1 to 10, and in certain embodiments, and an integer from 1 to 5. In addition, in certain embodiments, n may be any integer from 1 to 60.

In certain embodiments of Formula (1) and Formula (2), each p is independently selected from 2, 3, 4, 5, and 6. In certain embodiments, each p is the same and is 2, 3, 4, 5, or 6.

In certain embodiments, a sulfone-containing polythioether is selected from a sulfone-containing polythioether adduct of Formula (3), a sulfone-containing polythioether adduct of Formula (3a), and a combination thereof:

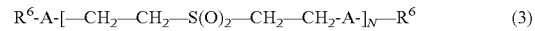

R$^6$-A-[—CH$_2$—CH$_2$—S(O)$_2$—CH$_2$—CH$_2$-A-]$_N$—R$^6$     (3)

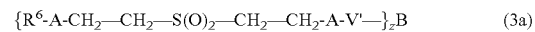

{R$^6$-A-CH$_2$—CH$_2$—S(O)$_2$—CH$_2$—CH$_2$-A-V'—}$_z$B     (3a)

wherein
N is an integer from 1 to 10;
each A is independently a moiety of Formula (2):

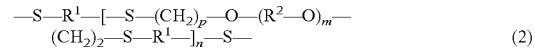

—S—R$^1$—[—S—(CH$_2$)$_p$—O—(R$^2$—O)$_m$—(CH$_2$)$_2$—S—R$^1$—]$_n$—S—     (2)

wherein:
  each R$^1$ independently is selected from C$_{2-10}$ alkanediyl, C$_{6-8}$ cycloalkanediyl, C$_{6-10}$ alkanecycloalkanediyl, C$_{5-8}$ heterocycloalkanediyl, and —[(—CHR$^3$—)$_s$—X—]$_q$—(—CHR$^3$—)$_r$—,
  wherein:
    s is an integer from 2 to 6;
    q is an integer from 1 to 5;
    r is an integer from 2 to 10;
    each R$^3$ is independently selected from hydrogen and methyl; and
    each X is independently selected from —O—, —S—, and —NR$^5$—, wherein R$^5$ is selected from hydrogen and methyl;
  each R$^2$ is independently selected from C$_{1-10}$ alkanediyl, C$_{6-8}$ cycloalkanediyl, C$_{6-14}$ alkanecycloalkanediyl, and —[(—CHR$^3$—)$_s$—X—]$_q$—(—CHR$^3$—)$_r$—, wherein s, q, r, R$^3$, and X are as defined for R$^1$;
  m is an integer from 0 to 50;
  n is an integer from 1 to 60; and
  p is an integer from 2 to 6;
  B represents a core of a z-valent, alkenyl-terminated polyfunctionalizing agent B(—V)$_z$ wherein:
    z is an integer from 3 to 6;
    each V is a group comprising a terminal alkenyl group; and
    each —V'— is derived from the reaction of —V with a thiol; and
  each R$^6$ is independently selected from hydrogen and a moiety having a terminal reactive group.

In certain embodiments of sulfone-containing polythioethers of Formula (3), N is 1, 2, 3, 4, 5, 6, 7, 8, 9, and in certain embodiments N is 10. In certain embodiments of sulfone-containing polymers of Formula (3), the molecular weight is from 200 Daltons to 2,000 Daltons. In certain embodiments, sulfone-containing polythioethers of Formula (3) comprise a combination of sulfone containing polythioethers of Formula (3) with different values for N. In certain embodiments of sulfone-containing polythioethers of Formula (3), N is 1.

In certain embodiments of sulfone-containing polythioethers of Formula (3) and Formula (3a), each $R^1$ is —[—(CHR$^3$)$_s$—X—]$_q$—(CHR$^3$)$_r$— wherein each X is independently selected from —O— and —S—.

In certain embodiments wherein $R^1$ is —[—(CHR$^3$)$_s$—X—]$_q$—(CHR$^3$)$_r$—, each X is —O— and in certain embodiments, each X is —S—. In certain embodiments, each $R^3$ is hydrogen.

In certain embodiments of sulfone-containing polythioethers of Formula (3) and Formula (3a), each $R^1$ is —[—(CH$_2$)$_s$—X—]$_q$—(CH$_2$)$_r$— wherein each X is independently selected from —O— and —S—. In certain embodiments wherein $R^1$ is —[—(CH$_2$)$_s$—X—]$_q$—(CH$_2$)$_r$—, each X is —O— and in certain embodiments, each X is —S—.

In certain embodiments of sulfone-containing polythioethers of Formula (3) and Formula (3a), each $R^1$ in Formula (2) is —[(—CH$_2$—)$_s$—X—]$_q$—(CH$_2$)$_r$—, where s is 2, X is O, q is 2, r is 2, $R^2$ is ethanediyl, m is 2, and n is 9.

In certain embodiments of sulfone-containing polythioethers of Formula (3) and Formula (3a), each $R^1$ is derived from DMDO and in certain embodiments, each $R^1$ is derived from DMDS.

In certain embodiments, each m is independently an integer from 1 to 3. In certain embodiments, each m is the same and is 1, 2, and in certain embodiments, 3.

In certain embodiments of sulfone-containing polythioethers of Formula (3) and Formula (3a), n is an integer from 1 to 30, an integer from 1 to 20, an integer from 1 to 10, and in certain embodiments, and integer from 1 to 5. In addition, in certain embodiments, n may be any integer from 1 to 60.

In certain embodiments of sulfone-containing polythioethers of Formula (3) and Formula (3a), each p is independently selected from 2, 3, 4, 5, and 6. In certain embodiments, each p is the same and is 2, 3, 4, 5, or 6.

In certain embodiments of sulfone-containing polythioethers of Formula (3) and Formula (3a), each $R^1$ is —[(—CH$_2$—)$_s$—X—]$_q$—(CH$_2$)$_r$—, where s is 2, X is —O—, q is 2, r is 2, $R^2$ is ethanediyl, m is 2, and n is 9.

In certain embodiments of sulfone-containing polythioethers of Formula (3) and Formula (3a), each $R^1$ is selected from C$_{2-6}$ alkanediyl and —[—(CHR$^3$)$_s$—X—]$_q$—(CHR$^3$)$_r$—.

In certain embodiments of sulfone-containing polythioethers of Formula (3) and Formula (3a), each $R^1$ is —[—(CHR$^3$)$_s$—X—]$_q$—(CHR$^3$)$_r$—, and in certain embodiments X is —O— and in certain embodiments, X is —S—.

In certain embodiments of sulfone-containing polythioethers of Formula (3) and Formula (3a), where $R^1$ is —[—(CHR$^3$)$_s$—X—]$_q$—(CHR$^3$)$_r$—, s is 2, r is 2, q is 1, and X is —S—; in certain embodiments, wherein s is 2, q is 2, r is 2, and X is —O—; and in certain embodiments, s is 2, r is 2, q is 1, and X is —O—.

In certain embodiments of sulfone-containing polythioethers of Formula (3) and Formula (3a), where $R^1$ is —[—(CHR$^3$)$_s$—X—]$_q$—(CHR$^3$)$_r$—, each $R^3$ is hydrogen, and in certain embodiments, at least one $R^3$ is methyl.

In certain embodiment of sulfone-containing polythioethers of Formula (3) and Formula (3a), each $R^1$ is the same, and in certain embodiments, at least one $R^1$ is different.

B(—V)$_z$ represents a polyfunctionalizing agent. The polyfunctionalizing agent may be a single type of polyfunctionalizing agent or a combination of different polyfunctionalizing agents, which may have the same or different functionalities. In certain embodiments, z is 3, 4, 5, or 6. Suitable polyfunctionalizing agents include trifunctionalizing agents, that is, compounds where z is 3. Suitable trifunctionalizing agents include, for example, triallyl cyanurate (TAC), modified-1,2,3-propanetrithiol, modified-isocyanurate-containing trithiols, and combinations thereof, as disclosed in U.S. Application Publication No. 2010/0010133 at paragraphs [0102]-[0105], the cited portion of which is incorporated herein by reference. Other useful polyfunctionalizing agents include trimethylolpropane trivinyl ether. Mixtures of polyfunctionalizing agents may also be used. Suitable isocyanurate-containing functionalizing agents are disclosed, for example, In U.S. Application Publication No. 2011/0319559.

$R^6$ represents a moiety having a terminal reactive group. The terminal reactive group can be selected as suitable for a particular curing chemistry. For example, in certain embodiments, each $R^6$ is the same and the reactive group is selected from —SH, —CH═CH$_2$, —NH$_2$, —OH, an epoxy group, a trialkylsilane group, a silyl group, —N═C═O, and a Michael acceptor group. The use a particular curing chemistry can be selected to tailor, for example, the curing time of a composition, the application method, surface compatibility, shelf life, pot life, and/or the properties of the cured sealant composition. For example, in certain embodiments, a sulfone-containing polythioether of Formula (3) and/or Formula (3a) is thiol-terminated and $R^6$ is hydrogen or a moiety terminated in a thiol group.

In certain embodiments, $R^6$ is hydrogen and the sulfone-containing polythioether adducts of Formula (3) and Formula (3a) are thiol-terminated.

In certain embodiments, the sulfone-containing polythioethers of Formula (3) and Formula (3a) are thiol-terminated, e.g., each $R^6$ is hydrogen, and can be referred to an uncapped sulfone-containing polythioether. In certain embodiments, an uncapped sulfone-containing polythioether is a liquid at room temperature. Moreover, in certain embodiments, an uncapped sulfone-containing polythioether has a viscosity, at 100% solids, of no more than 500 poise, such as 10-300 or, in some cases, 100-200 poise at a temperature of about 25° C. and a pressure of about 760 mm Hg determined according to ASTM D-2849 §79-90 measured using a Brookfield CAP 2000 viscometer. Any endpoint within the foregoing ranges can also be used. In certain embodiments, an uncapped sulfone-containing polythioether has a number average molecular weight of 300 to 10,000 grams per mole, such as 1,000 to 8,000 grams per mole, the molecular weight being determined, for example, by gel permeation chromatography using a polystyrene standard. Any endpoints within the foregoing ranges can also be used. In certain embodiments, the $T_g$ of an uncapped sulfone-containing polythioether is not higher than −55° C., such as not higher than −60° C.

In certain embodiments, a sulfone-containing polythioether may be capped to adapt the sulfone-containing polythioether for use with different curing chemistries.

Polythioether adducts of Formula (3) and Formula (3a) in which $R^6$ is a moiety having a terminal reactive group may be prepared by capping the corresponding thiol-terminated sulfone-containing polythioether adduct of Formula (3) and Formula (3a) wherein each $R^6$ is hydrogen with a moiety having a terminal reactive group and a group reactive with a thiol group. Capped analogs of polythioethers and methods of preparing capped analogs of polythioethers useful in aerospace sealant applications are disclosed, for example, in U.S. Pat. No. 6,172,179 and in U.S. Application Publication No. 2011/0319559.

In certain embodiments, a thiol-terminated sulfone-containing polythioether comprises the reaction product of reactants comprising:
(a) a thiol-terminated polythioether adduct selected from a thiol-terminated polythioether adduct of Formula (4), a thiol-terminated polythioether adduct of Formula (4a), and a combination thereof:

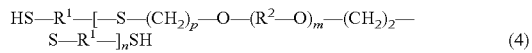

$$HS—R^1—[—S—(CH_2)_p—O—(R^2—O)_m—(CH_2)_2—S—R^1—]_nSH \quad (4)$$

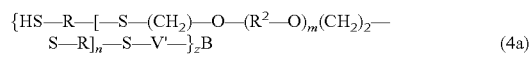

$$\{HS—R—[—S—(CH_2)_p—O—(R^2—O)_m(CH_2)_2—S—R]_n—S—V'—\}_zB \quad (4a)$$

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and $—[(—CHR^3—)_s—X—]_q—(—CHR^3—)_r—$,
wherein:
s is an integer from 2 to 6;
q is an integer from 1 to 5;
r is an integer from 2 to 10;
each $R^3$ is independently selected from hydrogen and methyl; and
each X is independently selected from —O—, —S—, and —NR$^5$—, wherein $R^5$ is selected from hydrogen and methyl;
each $R^2$ is independently selected from $C_{1-10}$ alkanediyl, $C_{6-8}$ cycloalkanediyl, $C_{6-14}$ alkanecycloalkanediyl, and $—[(—CHR^3—)_s—X—]_q—(CHR^3—)_r—$, wherein s, q, r, $R^3$, and X are as defined for $R^1$;
m is an integer from 0 to 50;
n is an integer from 1 to 60;
p is an integer from 2 to 6; and
B represents a core of a z-valent, alkenyl-terminated polyfunctionalizing agent $B(—V)_z$ wherein:
z is an integer from 3 to 6; and
each V is a group comprising a terminal alkenyl group; and
each —V'— is derived from the reaction of —V with a thiol; and
(b) a sulfone of Formula (5):

$$CH_2=CH—S(O)_2—CH=CH_2 \quad (5).$$

In certain embodiments of thiol-terminated polyethers of Formula (4) and Formula (4a), each $R^1$ is $—[—(CHR^3)_s—X—]_q—(CHR^3)_r—$ wherein each X is independently selected from —O— and —S—.

In certain embodiments wherein $R^1$ is $—[—(CHR^3)_s—X—]_q—(CHR^3)_r—$, each X is —O— and in certain embodiments, each X is —S—. In certain embodiments, each $R^3$ is hydrogen.

In certain embodiments of thiol-terminated polythioethers of Formula (4) and Formula (4a), each $R^1$ is $—[—(CH_2)_s—X—]_q—(CH_2)_r—$ wherein each X is independently selected from —O— and —S—. In certain embodiments wherein $R^1$ is $—[—(CH_2)_s—X—]_q—(CH_2)_r—$, each X is —O— and in certain embodiments, each X is —S—.

In certain embodiments of thiol-terminated polythioethers of Formula (4) and Formula (4a), each $R^1$ in Formula (2) is $—[(CH_2)_p—X—]_q—(CH_2)_r—$, where s is 2, X is O, q is 2, r is 2, $R^2$ is ethanediyl, m is 2, and n is 9.

In certain embodiments of thiol-terminated polythioethers of Formula (4) and Formula (4a), each $R^1$ is derived from DMDO and in certain embodiments, each $R^1$ is derived from DMDS.

In certain embodiments of thiol-terminated polythioethers of Formula (4) and Formula (4a), each m is independently an integer from 1 to 3. In certain embodiments, each m is the same and is 1, 2, and in certain embodiments, 3.

In certain embodiments of thiol-terminated polythioethers of Formula (4) and Formula (4a), n is an integer from 1 to 30, an integer from 1 to 20, an integer from 1 to 10, and in certain embodiments, and integer from 1 to 5. In addition, in certain embodiments, n may be any integer from 1 to 60.

In certain embodiments of thiol-terminated polythioethers of Formula (4) and Formula (4a), each p is independently selected from 2, 3, 4, 5, and 6. In certain embodiments, each p is the same and is 2, 3, 4, 5, or 6.

In certain embodiments of thiol-terminated polythioethers of Formula (4) and Formula (4a), $R^1$ is derived from DMDO, $R^2$ is derived from a divinyl ether, and the polyfunctionalizing agent is TAC.

A sulfone of Formula (5) is also known as divinyl sulfone.

Thiol-terminated polythioether adducts of Formula (4) and Formula (4a) and a sulfone of Formula (5) may be reacted in the presence of a base catalyst such as an amine catalyst. Examples of suitable amine catalysts include, for example, triethylenediamine (1,4-diazabicyclo[2.2.2]octane, DABCO), dimethylcyclohexylamine (DMCHA), dimethylethanolamine (DMEA), bis-(2-dimethylaminoethyl) ether, N-ethylmorpholine, triethylamine, 1,8-diazabicyclo [5.4.0]undecene-7 (DBU), pentamethyldiethylenetriamine (PMDETA), benzyldimethylamine (BDMA), N,N,N'-trimethyl-N'-hydroxyethyl-bis(aminoethyl)ether, and N'-(3-(dimethylamino)propyl)-N,N-dimethyl-1,3-propanediamine.

In certain embodiments, a sulfone-containing polythioether adduct provided by the present disclosure is characterized by a mercaptan equivalent weight (MEW) from about 400 to about 4,000.

Various methods can be used to prepare thiol-terminated polythioethers of Formula (4) and Formula (4a). Examples of suitable thiol-terminated polythioethers, and methods for their production, are described in U.S. Pat. No. 6,172,179 at col. 2, line 29 to col. 4, line 22; col. 6, line 39 to col. 10, line 50; and col. 11, lines 65 to col. 12, line 22, the cited portions of which are incorporated herein by reference. Such thiol-terminated polythioethers may be difunctional, that is, linear polymers having two terminal thiol groups, or polyfunctional, that is, branched polymers have three or more terminal thiol groups. Suitable thiol-terminated polythioethers are commercially available, for example, as Permapol® P3.1E, from PRC-DeSoto International Inc., Sylmar, Calif.

In certain embodiments, a thiol-terminated polythioether can be prepared by reacting a polythiol and a diene such as a divinyl ether, and the respective amounts of the reactants used to prepare the polythioethers are chosen to yield terminal thiol groups. Thus, in some cases, (n or >n, such as n+1) moles of a polythiol, such as a dithiol or a mixture of at least two different dithiols and about 0.05 to 1 moles, such as 0.1 to 0.8 moles, of a thiol-terminated polyfunctionalizing agent may be reacted with (n) moles of a diene, such as a divinyl ether, or a mixture of at least two different dienes, such as a divinyl ether. In certain embodiments, a thiol-terminated polyfunctionalizing agent is present in the reaction mixture in an amount sufficient to provide a thiol-terminated polythioether having an average functionality of from 2.05 to 3, such as 2.1 to 2.8.

The reaction used to make a thiol-terminated polythioether may be catalyzed by a free radical catalyst. Suitable free radical catalysts include azo compounds, for example azobisnitrile compounds such as azo(bis)isobutyronitrile (AIBN); organic peroxides, such as benzoyl peroxide and t-butyl peroxide; and inorganic peroxides, such as hydrogen peroxide. The reaction can also be effected by irradiation with ultraviolet light either with or without a radical initiator/photosensitizer. Ionic catalysis methods, using either inorganic or organic bases, e.g., triethylamine, may also be used.

Suitable thiol-terminated polythioethers may be produced by reacting a divinyl ether or mixtures of divinyl ethers with an excess of dithiol or a mixtures of dithiols.

Thus, in certain embodiments, a thiol-terminated polythioether comprises the reaction product of reactants comprising:

(a) a dithiol of Formula (8):

$$HS-R^1-SH \qquad (8)$$

wherein:
R$^1$ is selected from C$_{2-6}$ alkanediyl, C$_{6-8}$ cycloalkanediyl, C$_{6-10}$ alkanecycloalkanediyl, C$_{5-8}$ heterocycloalkanediyl, and —[—(CHR$^3$)$_s$—X—]$_q$—(CHR$^3$)$_r$—; wherein:
each R$^3$ is independently selected from hydrogen and methyl;
each X is independently selected from —O—, —S—, —NH—, and —NR— wherein R is selected from hydrogen and methyl;
s is an integer from 2 to 6;
q is an integer from 1 to 5; and
r is an integer from 2 to 10; and (b) a divinyl ether of Formula (9):

$$CH_2=CH-O-[-R^2-O-]_m-CH=CH_2 \qquad (9)$$

wherein:
each R$^2$ is independently selected from C$_{1-10}$ alkanediyl, C$_{6-8}$ cycloalkanediyl, C$_{6-14}$ alkanecycloalkanediyl, and —[(CHR$^3$—)$_s$—X—]$_q$—(CHR$^3$—)$_r$—, wherein s, q, r, R$^3$, and X are as defined above;
m is an integer from 0 to 50;
n is an integer from 1 to 60; and
p is an integer from 2 to 6.

And, in certain embodiments, the reactants comprise (c) a polyfunctional compound such as a polyfunctional compound B(—V)$_z$, where B, —V, and z are as defined herein.

In certain embodiments, dithiols suitable for use in preparing thiol-terminated polythioethers include those having Formula (8), other dithiols disclosed herein, or combinations of any of the dithiols disclosed herein. In certain embodiments, a dithiol has the structure of Formula (8):

$$HS-R^1-SH \qquad (8)$$

wherein:
R$^1$ is selected from C$_{2-6}$ alkanediyl, C$_{6-8}$ cycloalkanediyl, C$_{6-10}$ alkanecycloalkanediyl, C$_{5-8}$ heterocycloalkanediyl, and —[—(CHR$^3$)$_s$—X—]$_q$—(CHR$^3$)$_r$—;
wherein:
each R$^3$ is independently selected from hydrogen and methyl;
each X is independently selected from —O—, —S—, and —NR$^5$— wherein R$^5$ is selected from hydrogen and methyl;
s is an integer from 2 to 6;
q is an integer from 1 to 5; and
r is an integer from 2 to 10.

In certain embodiments of a dithiol of Formula (8), R$^1$ is —[—(CHR$^3$)$_s$—X—]$_q$—(CHR$^3$)$_r$—.

In certain embodiments of a compound of Formula (8), X is selected from —O— and —S—, and thus —[—(CHR$^3$)$_s$—X—]$_q$—(CHR$^3$)$_r$— in Formula (8) is —[(CHR$^3$—)$_s$—O—]$_q$—(CHR$^3$)$_r$— or —[(—CHR$^3{}_2$—)$_s$—S—]$_q$—(CHR$^3$)$_r$—. In certain embodiments, p and r are equal, such as where p and r are both two.

In certain embodiments of a dithiol of Formula (8), R$^1$ is selected from C$_{2-6}$ alkanediyl and —[—(CHR$^3$)$_s$—X—]$_q$—(CHR$^3$)$_r$—.

In certain embodiments of a dithiol of Formula (8), R$^1$ is —[—(CHR$^3$)$_s$—X—]$_q$—(CHR$^3$)$_r$—, and in certain embodiments X is —O—, and in certain embodiments, X is —S—.

In certain embodiments where R$^1$ is —[—(CHR$^3$)$_s$—X—]$_q$—(CHR$^3$)$_r$—, s is 2, r is 2, q is 1, and X is —S—; in certain embodiments, wherein s is 2, q is 2, r is 2, and X is —O—; and in certain embodiments, s is 2, r is 2, q is 1, and X is —O—.

In certain embodiments where R$^1$ is —[—(CHR$^3$)$_s$—X—]$_q$—(CHR$^3$)$_r$—, each R$^3$ is hydrogen, and in certain embodiments, at least one R$^3$ is methyl.

Examples of suitable dithiols include, for example, 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A polythiol may have one or more pendant groups selected from a lower (e.g., C$_{1-6}$) alkyl group, a lower alkoxy group, and a hydroxyl group. Suitable alkyl pendant groups include, for example, C$_{1-6}$ linear alkyl, C$_{3-6}$ branched alkyl, cyclopentyl, and cyclohexyl.

Other examples of suitable dithiols include dimercaptodiethylsulfide (DMDS) (in Formula (8), R$^1$ is —[(CH$_2$—)$_s$—X—]$_q$—(CH$_2$)$_r$—, wherein s is 2, r is 2, q is 1, and X is —S—); dimercaptodioxaoctane (DMDO) (in Formula (8), R$^1$ is —[(CH$_2$—)$_s$—X—]$_q$—(CH$_2$)$_r$—, wherein s is 2, q is 2, r is 2, and X is —O—); and 1,5-dimercapto-3-oxapentane (in Formula (8), R$^1$ is —[(—CH$_2$—)$_s$—X—]$_q$—(CH$_2$)$_r$—, wherein s is 2, r is 2, q is 1, and X is —O—). It is also possible to use dithiols that include both heteroatoms in the carbon backbone and pendant alkyl groups, such as methyl groups. Such compounds include, for example, methyl-substituted DMDS, such as HS—CH$_2$CH(CH$_3$)—S—CH$_2$CH$_2$—SH, HS—CH(CH$_3$)CH$_2$—S—CH$_2$CH$_2$—SH and dimethyl substituted DMDS, such as HS—CH$_2$CH(CH$_3$)—S—CHCH$_3$CH$_2$—SH and HS—CH(CH$_3$)CH$_2$—S—CH$_2$CH(CH$_3$)—SH.

Suitable divinyl ethers for preparing polythioethers and polythioether adducts include, for example, divinyl ethers of Formula (9):

$$CH_2=CH-O-(-R^2-O-)_mCH=CH_2 \qquad (9)$$

where R$^2$ in Formula (9) is selected from a C$_{2-6}$ n-alkanediyl group, a C$_{3-6}$ branched alkanediyl group, a C$_{6-8}$ cycloalkanediyl group, a C$_{6-10}$ alkanecycloalkanediyl group, and —[(CH$_2$—)$_s$—O—]$_q$—(CH$_2$—)$_r$—, where s is an integer ranging from 2 to 6, q is an integer from 1 to 5, and r is an integer from 2 to 10. In certain embodiments of a divinyl ether of Formula (9), R$^2$ is a C$_{2-6}$ n-alkanediyl group, a C$_{3-6}$ branched alkanediyl group, a C$_{6-8}$ cycloalkanediyl group, a C$_{6-10}$ alkanecycloalkanediyl group, and in certain embodiments, —[(—CH$_2$—)$_s$—O—]$_q$—(—CH$_2$—)$_r$—.

Suitable divinyl ethers include, for example, compounds having at least one oxyalkanediyl group, such as from 1 to 4 oxyalkanediyl groups, i.e., compounds in which m in Formula (9) is an integer ranging from 1 to 4. In certain embodiments, m in Formula (9) is an integer ranging from 2 to 4. It is also possible to employ commercially available divinyl ether mixtures that are characterized by a non-integral average value for the number of oxyalkanediyl units per molecule. Thus, m in Formula (9) can also take on rational number values ranging from 0 to 10.0, such as from 1.0 to 10.0, from 1.0 to 4.0, or from 2.0 to 4.0.

Examples of suitable vinyl ethers include, for example, divinyl ether, ethylene glycol divinyl ether (EG-DVE) ($R^2$ in Formula (9) is ethanediyl and m is 1), butanediol divinyl ether (BD-DVE) ($R^2$ in Formula (9) is butanediyl and m is 1), hexanediol divinyl ether (HD-DVE) ($R^2$ in Formula (9) is hexanediyl and m is 1), diethylene glycol divinyl ether (DEG-DVE) ($R^2$ in Formula (9) is ethanediyl and m is 2), triethylene glycol divinyl ether ($R^2$ in Formula (9) is ethanediyl and m is 3), tetraethylene glycol divinyl ether ($R^2$ in Formula (9) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such polyvinyl ether monomers. A polyvinyl ether may have one or more pendant groups selected from alkyl groups, hydroxyl groups, alkoxy groups, and amine groups.

In certain embodiments, divinyl ethers in which $R^2$ in Formula (9) is $C_{3-6}$ branched alkanediyl may be prepared by reacting a polyhydroxy compound with acetylene. Examples of divinyl ethers of this type include compounds in which $R^2$ in Formula (9) is an alkyl-substituted methanediyl group such as —CH(CH$_3$)—, for which $R^2$ in Formula (9) is ethanediyl and m is 3.8) or an alkyl-substituted ethanediyl.

Other useful divinyl ethers include compounds in which $R^2$ in Formula (9) is polytetrahydrofuryl (poly-THF) or polyoxyalkanediyl, such as those having an average of about 3 monomer units.

Two or more types of polyvinyl ether monomers of Formula (9) may be used. Thus, in certain embodiments, two dithiols of Formula (8) and one polyvinyl ether monomer of Formula (9), one dithiol of Formula (8) and two polyvinyl ether monomers of Formula (9), two dithiols of Formula (8) and two divinyl ether monomers of Formula (9), and more than two compounds of one or both Formula (8) and Formula (9), may be used to produce a variety of thiol-terminated polythioethers.

In certain embodiments, a polyvinyl ether monomer comprises 20 to less than 50 mole percent of the reactants used to prepare a thiol-terminated polythioether, and in certain embodiments, 30 to less than 50 mole percent.

In certain embodiments provided by the present disclosure, relative amounts of dithiols and divinyl ethers are selected to yield polythioethers having terminal thiol groups. Thus, a dithiol of Formula (8) or a mixture of at least two different dithiols of Formula (8), are reacted with of a divinyl ether of Formula (9) or a mixture of at least two different divinyl ethers of Formula (9) in relative amounts such that the molar ratio of thiol groups to vinyl groups is greater than 1:1, such as 1.1 to 2.0:1.0.

The reaction between dithiols and divinyl ethers and/or polythiols and polyvinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be a free-radical catalyst, an ionic catalyst, or ultraviolet radiation. In certain embodiments, the catalyst does not comprise acidic or basic compounds, and does not produce acidic or basic compounds upon decomposition. Examples of free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts are alkyl peroxides, such as t-butyl peroxide. The reaction may also be effected by irradiation with ultraviolet light either with or without a cationic photoinitiating moiety.

Thiol-terminated polythioethers provided by the present disclosure may be prepared by combining at least one compound of Formula (8) and at least one compound of Formula (9) followed by addition of an appropriate catalyst, and carrying out the reaction at a temperature from 30° C. to 120° C., such as 70° C. to 90° C., for a time from 2 to 24 hours, such as 2 to 6 hours.

As disclosed herein, thiol-terminated polythioethers may comprise a polyfunctional polythioether, i.e., may have an average functionality of greater than 2.0. Suitable polyfunctional thiol-terminated polythioethers include, for example, those having the structure of Formula (4a):

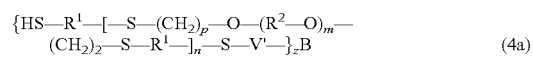

$$\{HS-R^1-[-S-(CH_2)_p-O-(R^2-O)_m-(CH_2)_2-S-R^1-]_n-S-V'-\}_zB \quad (4a)$$

wherein z has an average value of greater than 2.0, and, in certain embodiments, a value between 2 and 3, a value between 2 and 4, a value between 3 and 6, and in certain embodiments, is an integer from 3 to 6.

Polyfunctionalizing agents suitable for use in preparing such polyfunctional thiol-terminated polymers include trifunctionalizing agents, that is, compounds where z is 3. Suitable trifunctionalizing agents include, for example, triallyl cyanurate (TAC), 1,2,3-propanetrithiol, isocyanurate-containing trithiols, and combinations thereof, as disclosed in U.S. Publication No. 2010/0010133 at paragraphs [0102]-[0105], the cited portion of which is incorporated herein by reference and isocyanurates as disclosed, for example, in U.S. Application Publication No. 2011/0319559. Other useful polyfunctionalizing agents include trimethylolpropane trivinyl ether, and the polythiols described in U.S. Pat. Nos. 4,366,307; 4,609,762; and 5,225,472. Mixtures of polyfunctionalizing agents may also be used.

As a result, sulfone-containing polythioethers provided by the present disclosure may have a wide range of average functionality. For example, trifunctionalizing agents may afford average functionalities from 2.05 to 3.0, such as from 2.1 to 2.6. Wider ranges of average functionality may be achieved by using tetrafunctional or higher functionality polyfunctionalizing agents. Functionality may also be affected by factors such as stoichiometry, as will be understood by those skilled in the art.

Thiol-terminated polythioethers and sulfone-containing polythioethers having a functionality greater than 2.0 may be prepared in a manner similar to the difunctional thiol-terminated polythioethers described in U.S. Application Publication No. 2010/0010133, U.S. Application Publication No. 2011/0319559, and U.S. Pat. No. 6,172,179. In certain embodiments, polythioethers may be prepared by combining (i) one or more dithiols described herein, with (ii) one or more divinyl ethers described herein, and (iii) one or more polyfunctionalizing agents. The mixture may then be reacted, optionally in the presence of a suitable catalyst, to afford a thiol-terminated polythioether or sulfone-containing polythioether having a functionality greater than 2.0.

In certain embodiments, polythioethers including thiol-terminated polythioethers, sulfone-containing polythioethers, and capped analogs of any of the foregoing represent polythioethers having a molecular weight distribution. In certain embodiments, useful polythioethers can exhibit a number average molecular weight ranging from 500 Daltons to 20,000 Daltons, in certain embodiments, from 2,000 Daltons to 5,000 Daltons, and in certain embodiments, from 3,000 Daltons to 4,000 Daltons. In certain embodiments, useful polythioethers exhibit a polydispersity ($M_w/M_n$; weight average molecular weight/number average molecular weight) ranging from 1 to 20, and in certain embodiments, from 1 to 5. The molecular weight distribution of polythioethers may be characterized, for example, by gel permeation chromatography.

Methods

In general, thiol-terminated sulfone-containing polythioethers may be prepared by reacting a thiol-terminated polythioether or a mixture of thiol-terminated polythioethers with divinyl sulfone. In certain embodiments, a thiol-terminated sulfone-containing polythioether may be prepared by reacting a difunctional thiol-terminated polythioether or a mixture of difunctional thiol-terminated polythioethers with divinyl sulfone.

In certain embodiments, methods of preparing a thiol-terminated sulfone-containing polythioether adduct of Formula (6), comprise reacting (N+1) moles of a thiol-terminated polythioether of Formula (4) with (N) moles of a sulfone of Formula (5):

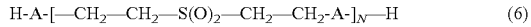

$$\text{H-A-[—CH}_2\text{—CH}_2\text{—S(O)}_2\text{—CH}_2\text{—CH}_2\text{-A-]}_N\text{—H} \qquad (6)$$

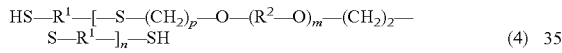

$$\text{HS—R}^1\text{—[—S—(CH}_2)_p\text{—O—(R}^2\text{—O)}_m\text{—(CH}_2)_2\text{—S—R}^1\text{—]}_n\text{—SH} \qquad (4)$$

$$\text{CH}_2\text{=CH—S(O)}_2\text{—CH=CH}_2 \qquad (5)$$

wherein:
N is an integer from 1 to 10;
each A is independently a moiety of Formula (2):

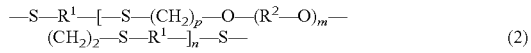

$$\text{—S—R}^1\text{—[—S—(CH}_2)_p\text{—O—(R}^2\text{—O)}_m\text{—(CH}_2)_2\text{—S—R}^1\text{—]}_n\text{—S—} \qquad (2)$$

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and —[(—CHR$^3$—)$_s$—X—]$_q$—(—CHR$^3$—)$_r$—,
wherein:
s is an integer from 2 to 6;
q is an integer from 1 to 5;
r is an integer from 2 to 10;
each $R^3$ is independently selected from hydrogen and methyl; and
each X is independently selected from —O—, —S—, and —NR$^5$—, wherein $R^5$ is selected from hydrogen and methyl; and
each $R^2$ is independently selected from $C_{1-10}$ alkanediyl, $C_{6-8}$ cycloalkanediyl, $C_{6-14}$ alkanecycloalkanediyl, and —[(CHR$^3$—)$_s$—X—]$_q$—(CHR$^3$—)$_r$—, wherein s, q, r, $R^3$, and X are as defined for $R^1$;
m is an integer from 0 to 50;
n is an integer from 1 to 60;
p is an integer from 2 to 6.

In certain embodiments of thiol-terminated sulfone-containing polythioethers of Formula (6), N is 1, 2, 3, 4, 5, 6, 7, 8, 9, and in certain embodiments N is 10. In certain embodiments of sulfone-containing polymers of Formula (6), the molecular weight is from 200 Daltons to 2,000 Daltons. In certain embodiments, thiol-terminated sulfone-containing polythioethers of Formula (6) comprise a combination of sulfone containing polythioethers of Formula (6) with different values for N. In certain embodiments of thiol-terminated sulfone-containing polythioethers of Formula (6), N is 1. Thus, in practice, when preparing a thiol-terminated sulfone-containing polythioether of Formula (6), the molar ratios of thiol-terminated polythioether to divinyl sulfone need not be a whole number such that thiol-terminated sulfone-containing polythioethers of Formula (6) represent a mixture of thiol-terminated sulfone-containing polythioethers having different values of N.

In certain embodiments, methods of preparing a thiol-terminated sulfone-containing polythioether adduct of Formula (6a) comprise reacting (z) moles of a thiol-terminated sulfone-containing polythioether of Formula (6) with one (1) mole of a polyfunctionalizing agent of Formula (7):

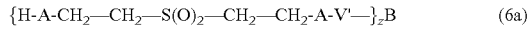

$$\{\text{H-A-CH}_2\text{—CH}_2\text{—S(O)}_2\text{—CH}_2\text{—CH}_2\text{-A-V'—}\}_z\text{B} \qquad (6a)$$

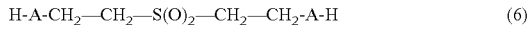

$$\text{H-A-CH}_2\text{—CH}_2\text{—S(O)}_2\text{—CH}_2\text{—CH}_2\text{-A-H} \qquad (6)$$

$$\text{B}\{V\}_z \qquad (7)$$

wherein:
each A is independently a moiety of Formula (2):

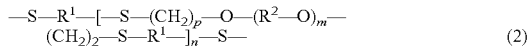

$$\text{—S—R}^1\text{—[—S—(CH}_2)_p\text{—O—(R}^2\text{—O)}_m\text{—(CH}_2)_2\text{—S—R}^1\text{—]}_n\text{—S—} \qquad (2)$$

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and —[(—CHR$^3$—)$_s$—X—]$_q$—(—CHR$^3$—)$_r$—,
wherein:
s is an integer from 2 to 6;
q is an integer from 1 to 5;
r is an integer from 2 to 10;
each $R^3$ is independently selected from hydrogen and methyl; and
each X is independently selected from —O—, —S—, and —NR$^5$—, wherein $R^5$ is selected from hydrogen and methyl;
each $R^2$ is independently selected from $C_{1-10}$ alkanediyl, $C_{6-8}$ cycloalkanediyl, $C_{6-14}$ alkanecycloalkanediyl, and —[(CHR$^3$—)$_s$—X—]$_q$—(CHR$^3$—)$_r$—, wherein s, q, r, $R^3$, and X are as defined for $R^1$;
m is an integer from 0 to 50;
n is an integer from 1 to 60; and
p is an integer from 2 to 6; and
B represents a core of a z-valent, alkenyl-terminated polyfunctionalizing agent B(—V)$_z$ wherein:
z is an integer from 3 to 6;
each V is a group comprising a terminal alkenyl group; and
each —V'— is derived from the reaction of —V with a thiol.

In certain embodiments, the reaction between a thiol-terminated sulfone-containing polythioether adduct and divinyl sulfone is performed in the presence of a catalyst such as an amine catalyst including, for example, any of those disclosed herein.

Thiol-terminated Sulfone-Containing Polythioether Prepolymers

Thiol-terminated sulfone-containing polythioether adducts provided by the present disclosure can be reacted with dialkenyl ethers and/or alkenyl-terminated polyfunctionalizing agents to provide thiol-terminated sulfone-containing polythioether prepolymers. Thiol-terminated sulfone-containing polythioether prepolymers may be combined with a curing agent to provide a curable composition such as a sealant composition.

For example, in certain embodiments a polythioether sulfone-containing polythioether prepolymer comprises the reaction product of reactants comprising:

(a) a thiol-terminated sulfone-containing polythioether adduct selected from an adduct of Formula (6), an adduct of Formula (6a), and a combination thereof:

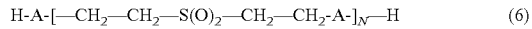

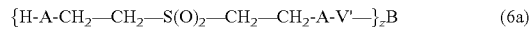

wherein
N is an integer from 1 to 10;
each A is independently a moiety of Formula (2):

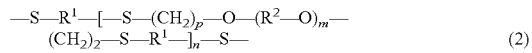

wherein:
each $R^1$ independently is selected from $C_{2-10}$ alkanediyl, $C_{6-8}$ cycloalkanediyl, $C_6$-10 alkanecycloalkanediyl, $C_{5-8}$ heterocycloalkanediyl, and —[(—CHR$^3$—)$_s$—X—]$_q$—(—CHR$^3$—)$_r$—,
wherein:
s is an integer from 2 to 6;
q is an integer from 1 to 5;
r is an integer from 2 to 10;
each $R^3$ is independently selected from hydrogen and methyl; and
each X is independently selected from —O—, —S—, and —NR$^5$—, wherein $R^5$ is selected from hydrogen and methyl;
each $R^2$ is independently selected from $C_{1-10}$ alkanediyl, $C_{6-8}$ cycloalkanediyl, $C_{6-14}$ alkanecycloalkanediyl, and —[(—CHR$^3$—)$_s$—X—]$_q$—(—CHR$^3$—)$_r$—, wherein s, q, r, $R^3$, and X are as defined for $R^1$;
m is an integer from 0 to 50;
n is an integer from 1 to 60; and
p is an integer from 2 to 6;
B represents a core of a z-valent, alkenyl-terminated polyfunctionalizing agent B(—V)$_z$ wherein:
z is an integer from 3 to 6;
each V is a group comprising a terminal alkenyl group; and
each —V'— is derived from the reaction of —V with a thiol; and
(b) a polyalkenyl compound.

In certain embodiments, a polyalkenyl compound is selected from a divinyl ether or a mixture of divinyl ethers including any of those disclosed herein, an alkenyl-terminated polyfunctionalizing agent, and a combination thereof.

In certain embodiments, (a) is an adduct of Formula (6), and (b) is a polyvinyl ether selected from a divinyl ether, an alkenyl-terminated polyfunctionalizing agent and a combination thereof.

In certain embodiments, (a) is an adduct of Formula (6), and (b) is a polyalkenyl ether selected from DEG-DE, TAC, and a combination thereof.

Capped Sulfone-Containing Polythioether Prepolymers

Sulfone-containing polythioethers may be adapted for use with a particular curing chemistry by capping or terminating a thiol-terminated sulfone-containing polythioether with a suitable functional group. Capped analogs of thiol-terminated polythioethers are disclosed, for example, in U.S. Pat. No. 6,172,179, U.S. Application Publication No. 2011/0319559.

For example, in certain embodiments, a sulfone-containing polythioether has terminal groups other than unreacted thiol groups, such as hydroxyl, alkenyl, isocyanate, amine, epoxy, a hydrolysable functional group such as an alkoxy silane group, a silyl group, a Michael acceptor group, or an epoxy group.

Capped analogs may be prepared by a number of methods known to those skilled in the art. For example, to obtain capped sulfone-containing polythioethers, a thiol-terminated sulfone-containing polythioether may be reacted with a compound having appropriate terminal groups.

To obtain an alkenyl-terminated sulfone-containing polythioether, a thiol-terminated sulfone-containing polythioether may be reacted with a compound containing a terminal alkenyl group and an isocyanate group such as a group derived from TMI, 2-isocyanatoethyl methacrylate, or allyl isocyanate, in the presence of dibutyltin dilaurate catalyst at about 76° C.

Silyl-terminated sulfone-containing polythioethers may be prepared, for example, by reacting a thiol-terminated sulfone-containing polythioether with an isocyanatoalkyltrialkoxysilane such as a 3-isocyanatopropyltrimethoxysilane or 3-isocyanatopropyltriethoxysilane in the presence of dibutyltin dilaurate at a temperature of about 76° C. to provide the corresponding silyl-terminated sulfone-containing polythioether.

Epoxy-terminated sulfone-containing polythioethers may be prepared, for example, by reacting a thiol-terminated sulfone-containing polythioether in the presence of a monoepoxide such as allyl glycidyl ether to provide the corresponding epoxy-terminated sulfone-containing polythioether.

Amine-terminated sulfone-containing polythioether may be prepared, for example, by reacting a thiol-terminated sulfone-containing polythioether with a monofunctional 4-amino butyl vinyl ether with a free-radical initiator Alternatively, an amine-terminated sulfone-containing polythioether may be obtained by reacting an isocyanate-terminated sulfone-containing polythioether with a diamine such as 4-(aminomethyl)aniline to provide the corresponding amine-terminated sulfone-containing polythioether. Amine-terminated sulfone-containing polythioether may also be obtained by reacting a thiol-terminated sulfone-containing polythioether with an amino-substituted benzoate such as ethyl-4-aminobenzoate in the presence of Bu$_2$SnO or NaOMe at elevated temperature to provide the corresponding amine-terminated sulfone-containing polythioether.

Isocyanate-terminated sulfone-containing polythioether may be prepared, for example, by reacting a thiol-terminated sulfone-containing polythioether with a diisocyanate such as TDI, Isonate™143L (polycarbodiimide-modified diphenylmethane diisocyanate), Desmodur® N3400 (1,3-diazetidine-2,4-dione, 1,3-bis(6-isocyanatohexyl)-), IPDI (isophorone diisocyanate), or Desmodur® W (H$_{12}$MDI) optionally in the presence of a catalyst such as dibutyltin dilaurate at a temperature from about 70° C. to about 80° C. Isocyanate-terminated sulfone-containing polythioether may be used as intermediates in the synthesis of other terminal-modified sulfone-containing polythioethers such as certain amine-terminated and thiol-terminated sulfone-containing polythioether.

Compositions

Compositions provided by the present disclosure may comprise one or more sulfone-containing polythioethers and/or more sulfone-containing polythioether prepolymers. Curable compositions further include a curing agent. Compositions may further include additives, catalysts, fillers, and/or other sulfur-containing polymers.

A suitable curing agent is selected to be reactive with the terminal groups of the sulfone-containing polythioether.

In certain embodiments in which a sulfone-containing polythioether or prepolymer is terminated with thiol groups a suitable curing agent is a polyepoxide. Examples of suitable polyepoxies include, for example, polyepoxide resins such as hydantoin diepoxide, diglycidyl ether of bisphenol-A, diglycidyl ether of bisphenol-F, Novolac® type epoxides such as DEN™ 438 (Dow Chemical Company), certain epoxidized unsaturated resins, and combinations of any of the foregoing. A polyepoxide refers to a compound having two or more reactive epoxy groups. In certain embodiments, an epoxy curing agent is selected from EPON™ 828 (Momentive Specialty Chemicals, Inc), DEN™ 431 (Dow Chemical Company), and a combination thereof. Examples of useful curing agents that are reactive with thiol groups include diepoxides.

In certain embodiments, a polyepoxy curing agent comprises an epoxy-functional polymer. Examples of suitable epoxy-functional polymers include the epoxy-functional polyformal polymers disclosed in U.S. application Ser. No. 13/050,988 and epoxy-functional polythioether polymers disclosed in U.S. Pat. No. 7,671,145. In general, when used as a curing agent, an epoxy-functional polymer has a molecular weight less than about 2,000 Daltons, less than about 1,500, Daltons, less than about 1,000 Daltons, and in certain embodiments, less than about 500 Daltons.

In certain embodiments, a polyepoxy may comprise about 0.5 wt % to about 20 wt % of the composition, from about 1 wt % to about 10 wt %, from about 2 wt % to about 8 wt %, from about 2 wt % to about 6 wt %, and in certain embodiments, from about 3 wt % to about 5 wt %, where wt % is based on the total solids weight of the composition.

In certain embodiments in which a sulfone-containing polythioether or prepolymer is terminated with thiol groups, a suitable curing agent is an unsaturated compound such as an acrylic or methacrylic ester of a polyol, unsaturated synthetic or naturally occurring resin compounds, triallyl cyanurate, and olefinic terminated derivatives of sulfur-containing compound such as polythioethers.

In certain embodiments, such as when amine and/or hydroxyl-terminated sulfone-containing polythioethers or prepolymers are used, compositions provided by the present disclosure comprise an isocyanate curing agent. Examples of suitable isocyanate curing agents include allyl isocyanate, 3-isopropenyl-α,α-dimethylbenzyl isocyanate, toluene diisocyanate, and combinations of any of the foregoing. Isocyanate curing agents are commercially available and include, for example, products under the tradenames Baydur® (Bayer MaterialScience), Desmodur® (Bayer MaterialScience), Solubond® (DSM), ECCO (ECCO), Vestanat® (Evonik), Irodur® (Huntsman), Rhodocoat™ (Perstorp), and Vanchem® (V.T. Vanderbilt). In certain embodiments, a polyisocyanate curing agent comprises isocyanate groups that are reactive with thiol groups and that are less reactive with Michael acceptor groups.

In certain embodiments, an isocyanate curing agent comprises an isocyanate-functional polymer. Examples of suitable isocyanate-functional polymers include the isocyanate-functional polyformal polymers disclosed in U.S. application Ser. No. 13/051,002. In general, when used as a curing agent, an isocyanate-functional polymer has a molecular weight less than about 2,000 Daltons, less than about 1,500, Daltons, less than about 1,000 Daltons, and in certain embodiments, less than about 500 Daltons.

In such compositions, an isocyanate curing agent may comprise about 0.5 wt % to about 20 wt % of the composition, from about 1 wt % to about 10 wt %, from about 2 wt % to about 8 wt %, from about 2 wt % to about 6 wt %, and in certain embodiments, from about 3 wt % to about 5 wt % of the composition, where wt % is based on the total solids weight of the composition.

In certain embodiments, such as when isocyanate-terminated sulfone-containing polythioethers or prepolymers are used, compositions provided by the present disclosure comprise an amine curing agent. Examples of useful curing agents that are reactive with isocyanate groups include diamines, polyamines, polythiols, and polyols, including those disclosed herein.

Examples of suitable amine curing agents include polyisocyanates having backbone groups chosen from urethane groups (—NH—C(O)—O—), thiourethane groups (—NH—C(O)—S—), thiocarbamate groups (—NH—C(S)—O—), dithiourethane linkages (—NH—C(S)—S—), and combinations of any of the foregoing.

In certain embodiments, such as when Michael acceptor-terminated sulfone-containing polythioethers or prepolymers are used, compositions provided by the present disclosure comprise a curing agent selected from a monomeric thiol, a polythiol, a polyamine, and a blocked polyamine.

Curing agents useful in compositions provided by the present disclosure include compounds that are reactive with the terminal groups of the sulfone-containing polythioether, such as compounds that are reactive with hydroxyl groups, alkenyl groups, epoxy groups, thiol groups, amine groups, or isocyanate groups.

Examples of useful curing agents that are reactive with hydroxyl groups include diisocyanates and polyisocyanates, examples of which are disclosed herein.

Examples of useful curing agents that are reactive with alkenyl groups include dithiols and polythiols, examples of which are disclosed herein.

Silyl-terminated sulfone-containing polythioether provided by the present disclosure can hydrolyze in the presence of water inducing self-polymerization via condensation. Catalysts for use with silyl-terminated sulfone-containing polythioether include organotitanium compounds such as tetraisopropoxy titanium, tetra-tert-butoxy titanium, titanium di(isopropoxy)bis(ethylacetoacetate), and titanium di(isopropoxy)bis(acetylacetoacetate); organic tin compounds dibutyltin dilaurate, dibutyltin bisacetylacetoacetate, and tin octylate; metal dicarboxylates such as lead dioctylate; organozirconium compounds such as zirconium tetraacetyl acetonate; and organoaluminum compounds such as aluminum triacetyl-acetonate. Other examples of suitable catalysts for moisture curing include diisopropoxy bis(ethyl acetoacetate)titanium, diisopropoxy bis(acetyl acetonate) titanium, and dibutoxy bis(methyl acetoacetate)titanium. It can be appreciated that because the curing agent for silyl-terminated sulfone-containing polythioether can be atmospheric moisture, it is not necessary to include a curing agent to a curable composition containing silyl-terminated sulfone-containing polythioether. Therefore, compositions comprising silyl-terminated sulfone-containing polythioether and a curing agent for the silyl group refer to atmospheric moisture.

Examples of useful curing agents that are reactive with terminal epoxy groups include amines such as diethylenetriamine (DTA), triethylenetetramine (TTA), tetraethylenepentamine (TEPA), diethylaminopropylamine (DEAPA), N-aminoethylpiperazine (N-AEP), isophoronediamine (IPDA), m-xylenediamine, diaminodiphenylmethane (DDM), diaminodiphenylsulfone (DDS); aromatic amines, ketimine; polyamines; polyamides; phenolic resins; anhydrides such phthalic anhydride, trimellitic anhydride, pyromellitic anhydride, benzophenone tetracarboxylic anhydride, ethylene glycol bistrimellitate, glycerol tristrimellitate, maleic anhydride, tetrahydrophthalic anhydride, methyltetrahydrophthalic anhydride, endomethylene tetrahydrophthalic anhydride; polymercaptans; polysulfides; ultraviolet curing agents such as diphenyliodinium hexafluorophosphate, triphenylsulfonium hexafluorophosphate; and other curing agents known to those skilled in the art.

Examples of useful curing agents that are reactive with amine groups include polymeric polyisocyanates, non-limiting examples of which include polyisocyanates having backbone linkages chosen from urethane linkages (—NH—C(O)—O—), thiourethane linkages (—NH—C(O)—S—), thiocarbamate linkages (—NH—C(S)—O—), dithiourethane linkages (—NH—C(S)—S—), and combinations of any of the foregoing.

Examples of useful curing agents that are reactive with isocyanate groups include diamines, polyamines, polythiols, and polyols, including those disclosed herein.

Compositions provided by the present disclosure may contain from about 90% to about 150% of the stoichiometric amount, from about 95% to about 125%, and in certain embodiments, from about 95% to about 105% of the amount of the selected curing agent(s).

Additional Sulfur-Containing Polymers

In certain embodiments, compositions provided by the present disclosure comprise, in addition to a sulfone-containing polythioether or prepolymer, or a reaction product of any one of the reactions disclosed herein, or a combination of any of the foregoing, one or more additional sulfur-containing polymers. A sulfur-containing polymer can be any polymer having at least one sulfur atom in the repeating unit, including, but not limited to, polymeric thiols, polythiols, thioethers, polythioethers, polyformals, and polysulfides. A "thiol," as used herein, refers to a compound comprising a thiol or mercaptan group, that is, an "SH" group, either as the sole functional group or in combination with other functional groups, such as hydroxyl groups, as is the case with, for example, thioglycerols. A polythiol refers to such a compound having more than one SH group, such as a dithiol or higher functionality thiol. Such groups are typically terminal and/or pendant such that they have an active hydrogen that is reactive with other functional groups. As used herein, the term "polysulfide" refers to any compound that comprises a sulfur-sulfur linkage (—S—S—). A polythiol can comprise both a terminal and/or pendant sulfur (—SH) and a non-reactive sulfur atom (—S— or —S—S—). Thus, the term polythiol generally encompasses polythioethers and polysulfides. Examples of additional sulfur-containing polymers useful in compositions provided by the present disclosure include, for example, those disclosed in U.S. Pat. Nos. 6,172,179, 6,509,418, and 7,009,032. In certain embodiments, compositions provided by the present disclosure comprise a polythioether having the structure:

—R$^1$—[—S—(CH$_2$)$_2$—O—[—R$^2$—O—]$_m$—(CH$_2$)$_2$—S—R$^1$—]$_n$— wherein R$^1$ is selected from a C$_{2-6}$ alkanediyl, C$_{6-8}$ cycloalkanediyl, C$_{6-10}$ cycloalkanealkanediyl, —[(—CH$_2$—)$_s$—X—]$_q$—(—CH$_2$—)$_r$—, and —[(—CH$_2$—)$_s$—X—]$_q$—(CH$_2$—)$_r$— in which at least one —CH$_2$— unit is substituted with a methyl group; R$^2$ is selected from C$_{2-6}$ alkanediyl, C$_{6-8}$ cycloalkanediyl, C$_{6-10}$ cycloalkanealkanediyl, and —[(CH$_2$—)$_s$—X—]$_q$—(—CH$_2$—)$_r$—; X is selected from O, S, and —NR$^5$—, where R$^5$ is selected from hydrogen and methyl; m is an integer from 0 to 10; n is an integer from 1 to 60; p is an integer from 2 to 6; q is an integer from 1 to 5, and r is an integer from 2 to 10. Such polythioethers are described in U.S. Pat. No. 6,172,179 at col. 2, line 29 to col. 4, line 34.

The one or more additional sulfur-containing polymers may be difunctional or multifunctional, for example, having from 3 to 6 terminal groups, or a mixture thereof.

In certain embodiments, compositions provided by the present disclosure comprise from about 10 wt % to about 90 wt % of a sulfur-containing polymer provided by the present disclosure, from about 20 wt % to about 80 wt %, from about 30 wt % to about 70 wt %, and in certain embodiments from about 40 wt % to about 60 wt %, where wt % is based on the total weight of all non-volatile components of the composition (i.e., the dry weight).

As used herein, the term polysulfide refers to a polymer that contains one or more sulfide linkages, i.e., —S$_x$— linkages, where x is from 2 to 4, in the polymer backbone and/or in pendant positions on the polymer chain. In certain embodiments, the polysulfide polymer will have two or more sulfur-sulfur linkages. Suitable polysulfides are commercially available, for example, from Akzo Nobel and Toray Fine Chemicals under the names Thiokol-LP and Thioplast®. Thioplast® products are available in a wide range of molecular weights ranging, for example, from less than 1,100 to over 8,000, with molecular weight being the average molecular weight in grams per mole. In some cases, the polysulfide has a number average molecular weight of 1,000 to 4,000. The crosslink density of these products also varies, depending on the amount of crosslinking agent used. The —SH content, i.e., thiol or mercaptan content, of these products can also vary. The mercaptan content and molecular weight of the polysulfide can affect the cure speed of the polymer, with cure speed increasing with molecular weight.

Polyformal prepolymers useful in aerospace sealant applications are disclosed, for example, in U.S. Publication No. 2012/0234205 and U.S. Publication No. 2012/0238707.

In certain embodiments, the sulfur-containing polymer is selected from a polythioether and a polysulfide, and a combination thereof. In certain embodiments a sulfur-containing polymer comprises a polythioether, and in certain embodiments, a sulfur-containing polymer comprises a polysulfide. A sulfur-containing polymer may comprise a mixture of different polythioethers and/or polysulfides, and the polythioethers and/or polysulfides may have the same or different functionality. In certain embodiments, a sulfur-containing polymer has an average functionality from 2 to 6, from 2 to 4, from 2 to 3, and in certain embodiments, from 2.05 to 2.5. For example, a sulfur-containing polymer can be selected from a difunctional sulfur-containing polymer, a trifunctional sulfur-containing polymer, and a combination thereof.

Compositions provided by the present disclosure may include one or more catalysts. A catalyst can be selected as appropriate for the curing chemistry employed. In certain embodiments, for example, when curing thiol-terminated sulfone-containing polythioethers or prepolymers and polyepoxides, the catalyst is an amine catalyst. A cure catalyst may be present in an amount from 0.1 to 5 weight percent, based on the total weight of the composition. Examples of suitable catalysts include 1,4-diaza-bicyclo[2.2.2]octane (DABCO®, commercially available from Air Products, Chemical Additives Division, Allentown, Pa.) and DMP-30® (an accelerant composition including 2,4,6-tris(dimethylaminomethyl)phenol.

In certain embodiments, compositions provided by the present disclosure comprise one or more than one adhesion promoters. A one or more additional adhesion promoter may be present in amount from 0.1 wt % to 15 wt % of a composition, less than 5 wt %, less than 2 wt %, and in certain embodiments, less than 1 wt %, based on the total dry weight of the composition. Examples of adhesion promoters include phenolics, such as Methylon® phenolic resin, and organosilanes, such as epoxy, mercapto or amino functional silanes, such as Silquest® A-187 and Silquest® A-1100. Other useful adhesion promoters are known in the art.

Compositions provided by the present disclosure may comprise one or more different types of filler. Suitable fillers include those commonly known in the art, including inorganic fillers, such as carbon black and calcium carbonate ($CaCO_3$), silica, polymer powders, and lightweight fillers. Suitable lightweight fillers include, for example, those described in U.S. Pat. No. 6,525,168. In certain embodiments, a composition includes 5 wt % to 60 wt % of the filler or combination of fillers, 10 wt % to 50 wt %, and in certain embodiments, from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst.

In certain embodiments, compositions provided by the present disclosure include low density filler particles. As used herein, low density, when used with reference to such particles means that the particles have a specific gravity of no more than 0.7, in certain embodiments no more than 0.25, and in certain embodiments, no more than 0.1. Suitable lightweight filler particles often fall within two categories—microspheres and amorphous particles. The specific gravity of microspheres may range from 0.1 to 0.7 and include, for example, polystyrene foam, microspheres of polyacrylates and polyolefins, and silica microspheres having particle sizes ranging from 5 to 100 microns and a specific gravity of 0.25 (Eccospheres®). Other examples include alumina/silica microspheres having particle sizes in the range of 5 to 300 microns and a specific gravity of 0.7 (Fillite®), aluminum silicate microspheres having a specific gravity of from about 0.45 to about 0.7 (Z-Light®), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of about 40 µm and a density of 0.135 g/cc (Henkel). Suitable fillers for decreasing the specific gravity of the composition include, for example, hollow microspheres such as Expancel® microspheres (available from AkzoNobel) or Dualite® low density polymer microspheres (available from Henkel). In certain embodiments, compositions provided by the present disclosure include lightweight filler particles comprising an exterior surface coated with a thin coating, such as those described in U.S. Publication No. 2010/0041839 at paragraphs [0016]-[0052], the cited portion of which is incorporated herein by reference.

In certain embodiments, a low density filler comprises less than 2 wt % of a composition, less than 1.5 wt %, less than 1.0 wt %, less than 0.8 wt %, less than 0.75 wt %, less than 0.7 wt % and in certain embodiments, less than 0.5 wt % of a composition, where wt % is based on the total dry solids weight of the composition.

In certain embodiments, compositions provided by the present disclosure comprise at least one filler that is effective in reducing the specific gravity of the composition. In certain embodiments, the specific gravity of a composition is from 0.8 to 1, 0.7 to 0.9, from 0.75 to 0.85, and in certain embodiments, is 0.8. In certain embodiments, the specific gravity of a composition is less than about 0.9, less than about 0.8, less than about 0.75, less than about 0.7, less than about 0.65, less than about 0.6, and in certain embodiments, less than about 0.55.

In certain embodiments, compositions provided by the present disclosure comprise an electrically conductive filler. Electrical conductivity and EMI/RFI shielding effectiveness can be imparted to composition by incorporating conductive materials within the polymer. The conductive elements can include, for example, metal or metal-plated particles, fabrics, meshes, fibers, and combinations thereof. The metal can be in the form of, for example, filaments, particles, flakes, or spheres. Examples of metals include copper, nickel, silver, aluminum, tin, and steel. Other conductive materials that can be used to impart EMI/RFI shielding effectiveness to polymer compositions include conductive particles or fibers comprising carbon or graphite. Conductive polymers such as polythiophenes, polypyrroles, polyaniline, poly(p-phenylene) vinylene, polyphenylene sulfide, polyphenylene, and polyacetylene can also be used.

Examples of electrically non-conductive fillers include materials such as, but not limited to, calcium carbonate, mica, polyamide, fumed silica, molecular sieve powder, microspheres, titanium dioxide, chalks, alkaline blacks, cellulose, zinc sulfide, heavy spar, alkaline earth oxides, alkaline earth hydroxides, and the like. Fillers also include high band gap materials such as zinc sulfide and inorganic barium compounds. In certain embodiments, an electrically conductive base composition can comprise an amount of electrically non-conductive filler ranging from 2 wt % to 10 wt % based on the total weight of the base composition, and in certain embodiments, can range from 3 wt % to 7 wt %. In certain embodiments, a curing agent composition can comprise an amount of electrically non-conductive filler ranging from less than 6 wt % and in certain embodiments ranging from 0.5% to 4% by weight, based on the total weight of the curing agent composition.

Fillers used to impart electrical conductivity and EMI/RFI shielding effectiveness to polymer compositions are well known in the art. Examples of electrically conductive fillers include electrically conductive noble metal-based fillers such as pure silver; noble metal-plated noble metals such as silver-plated gold; noble metal-plated non-noble metals such as silver plated cooper, nickel or aluminum, for example, silver-plated aluminum core particles or platinum-plated copper particles; noble-metal plated glass, plastic or ceramics such as silver-plated glass microspheres, noble-metal plated aluminum or noble-metal plated plastic microspheres; noble-metal plated mica; and other such noble-metal conductive fillers. Non-noble metal-based materials can also be used and include, for example, non-noble metal-plated non-noble metals such as copper-coated iron particles or nickel plated copper; non-noble metals, e.g., copper, aluminum, nickel, cobalt; non-noble-metal-plated-non-metals, e.g., nickel-plated graphite and non-metal materials such as carbon black and graphite. Combinations of electrically conductive fillers can also be used to meet the desired conductivity, EMI/RFI shielding effectiveness, hardness, and other properties suitable for a particular application.

The shape and size of the electrically conductive fillers used in the compositions of the present disclosure can be any appropriate shape and size to impart EMI/RFI shielding effectiveness to the cured composition. For example, fillers can be of any shape that is generally used in the manufacture of electrically conductive fillers, including spherical, flake, platelet, particle, powder, irregular, fiber, and the like. In certain sealant compositions of the disclosure, a base composition can comprise Ni-coated graphite as a particle, powder or flake. In certain embodiments, the amount of Ni-coated graphite in a base composition can range from 40 wt % to 80 wt %, and in certain embodiments can range from 50 wt % to 70 wt %, based on the total weight of the base composition. In certain embodiments, an electrically conductive filler can comprise Ni fiber. Ni fiber can have a diameter ranging from 10 µm to 50 µm and have a length ranging from 250 µm to 750 µm. A base composition can comprise, for example, an amount of Ni fiber ranging from 2 wt % to 10 wt %, and in certain embodiments, from 4 wt % to 8 wt %, based on the total weight of the base composition.

Carbon fibers, particularly graphitized carbon fibers, can also be used to impart electrical conductivity to compositions of the present disclosure. Carbon fibers formed by vapor phase pyrolysis methods and graphitized by heat treatment and which are hollow or solid with a fiber diameter ranging from 0.1 micron to several microns, have high electrical conductivity. As disclosed in U.S. Pat. No. 6,184,280, carbon microfibers, nanotubes or carbon fibrils having an outer diameter of less than 0.1 µm to tens of nanometers can be used as electrically conductive fillers. An example of graphitized carbon fiber suitable for conductive compositions of the present disclosure include PANEX 30MF (Zoltek Companies, Inc., St. Louis, Mo.), a 0.921 µm diameter round fiber having an electrical resistivity of 0.00055 Ω-cm.

The average particle size of an electrically conductive filler can be within a range useful for imparting electrical conductivity to a polymer-based composition. For example, in certain embodiments, the particle size of the one or more fillers can range from 0.25 µm to 250 m, in certain embodiments can range from 0.25 µm to 75 µm, and in certain embodiments can range from 0.25 µm to 60 µm. In certain embodiments, composition of the present disclosure can comprise Ketjenblack® EC-600 JD (Akzo Nobel, Inc., Chicago, Ill.), an electrically conductive carbon black characterized by an iodine absorption of 1000-11500 mg/g (J0/84-5 test method), and a pore volume of 480-510 cm$^{3/100}$ gm (DBP absorption, KTM 81-3504). In certain embodiments, an electrically conductive carbon black filler is Black Pearls® 2000 (Cabot Corporation, Boston, Mass.).

In certain embodiments, electrically conductive polymers can be used to impart or modify the electrical conductivity of compositions of the present disclosure. Polymers having sulfur atoms incorporated into aromatic groups or adjacent to double bonds, such as in polyphenylene sulfide, and polythiophene, are known to be electrically conductive. Other electrically conductive polymers include, for example, polypyrroles, polyaniline, poly(p-phenylene) vinylene, and polyacetylene. In certain embodiments, the sulfur-containing polymers forming a base composition can be polysulfides and/or polythioethers. As such, the sulfur-containing polymers can comprise aromatic sulfur groups and sulfur atoms adjacent to conjugated double bonds such as vinylcyclohexene-dimercaptodioxaoctane groups, to enhance the electrical conductivity of the compositions of the present disclosure.

Compositions of the present disclosure can comprise more than one electrically conductive filler and the more than one electrically conductive filler can be of the same or different materials and/or shapes. For example, a sealant composition can comprise electrically conductive Ni fibers, and electrically conductive Ni-coated graphite in the form of powder, particles or flakes. The amount and type of electrically conductive filler can be selected to produce a sealant composition which, when cured, exhibits a sheet resistance (four-point resistance) of less than 0.50 $\Omega/cm^2$, and in certain embodiments, a sheet resistance less than 0.15 $\Omega/cm^2$. The amount and type of filler can also be selected to provide effective EMI/RFI shielding over a frequency range of from 1 MHz to 18 GHz for an aperture sealed using a sealant composition of the present disclosure.

Galvanic corrosion of dissimilar metal surfaces and the conductive compositions of the present disclosure can be minimized or prevented by adding corrosion inhibitors to the composition, and/or by selecting appropriate conductive fillers. In certain embodiments, corrosion inhibitors include strontium chromate, calcium chromate, magnesium chromate, and combinations thereof. U.S. Pat. Nos. 5,284,888 and 5,270,364 disclose the use of aromatic triazoles to inhibit corrosion of aluminum and steel surfaces. In certain embodiments, a sacrificial oxygen scavenger such as Zn can be used as a corrosion inhibitor. In certain embodiments, the corrosion inhibitor can comprise less than 10% by weight of the total weight of the electrically conductive composition. In certain embodiments, the corrosion inhibitor can comprise an amount ranging from 2% by weight to 8% by weight of the total weight of the electrically conductive composition. Corrosion between dissimilar metal surfaces can also be minimized or prevented by the selection of the type, amount, and properties of the conductive fillers comprising the composition.

In certain embodiments, a sulfone-containing polythioether and/or sulfone-containing polythioether prepolymer may comprise from about 50 wt % to about 90 wt % of a composition, from about 60 wt % to about 90 wt %, from about 70 wt % to about 90 wt %, and in certain embodiments, from about 80 wt % to about 90 wt % of the composition, where wt % is based on the total dry solids weight of the composition.

A composition may also include any number of additives as desired. Examples of suitable additives include plasticizers, pigments, surfactants, adhesion promoters, thixotropic agents, fire retardants, masking agents, and accelerators (such as amines, including 1,4-diaza-bicyclo[2.2.2]octane, DABCO®), and combinations of any of the foregoing. When used, the additives may be present in a composition in an amount ranging, for example, from about 0% to 60% by weight. In certain embodiments, additives may be present in a composition in an amount ranging from about 25% to 60% by weight.

Uses

Compositions provided by the present disclosure may be used, for example, in sealants, coatings, encapsulants, and potting compositions. A sealant includes a composition capable of producing a film that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. In certain embodiments, sealant compositions provided by the present disclosure are useful, e.g., as aerospace sealants and as linings for fuel tanks.

In certain embodiments, compositions, such as sealants, may be provided as multi-pack compositions, such as two-pack compositions, wherein one package comprises one or more thiol-terminated polythioethers provided by the present disclosure and a second package comprises one or more polyfunctional sulfur-containing epoxies provided by the present disclosure. Additives and/or other materials may be added to either package as desired or necessary. The two packages may be combined and mixed prior to use. In certain embodiments, the pot life of the one or more mixed thiol-terminated polythioethers and epoxies is at least 30 minutes, at least 1 hour, at least 2 hours, and in certain embodiments, more than 2 hours, where pot life refers to the period of time the mixed composition remains suitable for use as a sealant after mixing.

Compositions, including sealants, provided by the present disclosure may be applied to any of a variety of substrates. Examples of substrates to which a composition may be applied include metals such as titanium, stainless steel, and aluminum, any of which may be anodized, primed, organic-coated or chromate-coated; epoxy; urethane; graphite; fiberglass composite; Kevlar®; acrylics; and polycarbonates. In certain embodiments, compositions provided by the present disclosure may be applied to a coating on a substrate, such as a polyurethane coating.

Compositions provided by the present disclosure may be applied directly onto the surface of a substrate or over an underlayer by any suitable coating process known to those of ordinary skill in the art.

Furthermore, methods are provided for sealing an aperture utilizing a composition provided by the present disclosure. These methods comprise, for example, applying a composition provided by the present disclosure to a surface to seal an aperture, and curing the composition. In certain embodiments, a method for sealing an aperture comprises (a) applying a sealant composition provided by the present disclosure to one or more surfaces defining an aperture, (b) assembling the surfaces defining the aperture, and (c) curing the sealant, to provide a sealed aperture.

In certain embodiments, a composition may be cured under ambient conditions, where ambient conditions refers to a temperature from 20° C. to 25° C., and atmospheric humidity. In certain embodiments, a composition may be cured under conditions encompassing a temperature from a 0° C. to 100° C. and humidity from 0% relative humidity to 100% relative humidity. In certain embodiments, a composition may be cured at a higher temperature such as at least 30° C., at least 40° C., and in certain embodiments, at least 50° C. In certain embodiments, a composition may be cured at room temperature, e.g., 25° C. In certain embodiments, a composition may be cured upon exposure to actinic radiation, such as ultraviolet radiation. As will also be appreciated, the methods may be used to seal apertures on aerospace vehicles including aircraft and aerospace vehicles.

In certain embodiments, the composition achieves a tack-free cure in less than about 2 hours, less than about 4 hours, less than about 6 hours, less than about 8 hours, and in certain embodiments, less than about 10 hours, at a temperature of less than about 200° F.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within 24 hours to 30 hours, and 90% of full adhesion strength develops from 2 days to 3 days, following mixing and application to a surface. In general, full adhesion strength as well as other properties of cured compositions of the present disclosure becomes fully developed within 7 days following mixing and application of a curable composition to a surface.

Cured compositions disclosed herein, such as cured sealants, exhibit properties acceptable for use in aerospace applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in JRF for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aviation and aerospace applications are disclosed in AMS 3265B, the entirety of which is incorporated herein by reference. It is also desirable that, when cured, compositions of the present disclosure used in aviation and aircraft applications exhibit a percent volume swell not greater than 25% following immersion for one week at 60° C. (140° F.) and ambient pressure in JRF type 1. Other properties, ranges, and/or thresholds may be appropriate for other sealant applications.

In certain embodiments, therefore, compositions provided by the present disclosure are fuel-resistant. As used herein, the term "fuel resistant" means that a composition, when applied to a substrate and cured, can provide a cured product, such as a sealant, that exhibits a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification). Jet Reference Fluid JRF Type I, as employed for determination of fuel resistance, has the following composition: toluene: 28±1% by volume; cyclohexane (technical): 34±1% by volume; isooctane: 38±1% by volume; and tertiary dibutyl disulfide: 1±0.005% by volume (see AMS 2629, issued Jul. 1, 1989, §3.1.1 etc., available from SAE (Society of Automotive Engineers)).

In certain embodiments, compositions provided herein provide a cured product, such as a sealant, exhibiting a tensile elongation of at least 100% and a tensile strength of at least 400 psi when measured in accordance with the procedure described in AMS 3279, §3.3.17.1, test procedure AS5127/1, §7.7.

In certain embodiments, compositions provide a cured product, such as a sealant, that exhibits a lap shear strength of greater than 200 psi, such as at least 220 psi, at least 250 psi, and, in some cases, at least 400 psi, when measured according to the procedure described in SAE AS5127/1 paragraph 7.8.

In certain embodiments, a cured sealant comprising a composition provided by the present disclosure meets or exceeds the requirements for aerospace sealants as set forth in AMS 3277.

Apertures, including apertures of aerospace vehicles, sealed with compositions provided by the present disclosure are also disclosed.

In certain embodiments, an electrically conductive sealant composition provided by the present disclosure exhibits the following properties measured at room temperature following exposure at 500° F. for 24 hours: a surface resistivity of less than 1 ohms/square, a tensile strength greater than 200 psi, an elongation greater than 100%, and a cohesive failure of 100% measured according to MIL-C-27725.

In certain embodiments, a cured sealant provided by the present disclosure exhibits the following properties when cured for 2 days at room temperature, 1 day at 140° F., and 1 day at 200° F.: a dry hardness of 49, a tensile strength of 428 psi, and an elongation of 266%; and after 7 days in JRF, a hardness of 36, a tensile strength of 312 psi, and an elongation of 247%.

In certain embodiments, compositions provided by the present disclosure exhibit a Shore A hardness (7-day cure) greater than 10, greater than 20, greater than 30, and in certain embodiments, greater than 40; a tensile strength greater than 10 psi, greater than 100 psi, greater than 200 psi, and in certain embodiments, greater than 500 psi; an elongation greater than 100%, greater than 200%, greater than 500%, and in certain embodiments, greater than 1,000%; and a swell following exposure to JRF (7 days) less than 20%.

EXAMPLES

Embodiments provided by the present disclosure are further illustrated by reference to the following examples, which describe the synthesis, properties, and uses of certain sulfone-containing polythioethers and compositions comprising sulfone-containing polythioethers. It will be apparent to those skilled in the art that many modifications, both to materials, and methods, may be practiced without departing from the scope of the disclosure.

Example 1

Thiol-terminated Polythioether Adduct

In a 250-mL, 3-necked round bottom flask fitted with a thermal probe, a mechanical stirrer, and a nitrogen ($N_2$) inlet, 76.57 g of 1,8-dimercapto-3,6-dioxaoctane (DMDO) and 44.30 g of diethylene glycol divinyl ether were charged. The mixture was stirred stir at room temperature for 20 minutes. The mixture was then heated to 77° C. and 202 mg of Vazo™-67 (Dupont) was added. The reaction mixture was maintained at 77° C. for 8 hours. The progress of the reaction was monitored by mercaptan equivalent weight (MEW). The final MEW was 465.

Example 2

Thiol-terminated Sulfone-containing Polythioether Adduct

In a 250-mL, 3-necked round bottom flask fitted with a thermal probe, a mechanical stirrer, and a nitrogen ($N_2$) inlet, 120.86 g of the adduct of Example 1 and 0.075 g of Polycat® DBU (Air Products and Chemicals) were added. Then, 7.68 g of divinyl sulfone (available from Sigma Aldrich) was slowly added to the flask. The reaction was maintained for 5 hours in a cold water bath. The progress of the reaction was monitored by mercaptan equivalent weight (MEW). The final MEW was 970.

Example 3

Thiol-terminated Sulfone-containing Polythioether Prepolymer

In a 250-mL, 3-necked round bottom flask fitted with a thermal probe, a mechanical stirrer, and a nitrogen ($N_2$) inlet, 1.99 g of triallyl cyanurate (TAC), 1.88 g of diethylene glycol divinyl ether, and 128.14 g of Example 2 adduct were charged. The mixture was stirred at room temperature for 20 minutes. The mixture was then heated to 77° C., and 271 mg of Vazo™-67 (Dupont) was added. The reaction mixture was maintained at 77° C. for 19 hours. The progress of the reaction was monitored by mercaptan equivalent weight (MEW). The final MEW was 1591.

Example 4

Sulfone-containing Polythioether Sealant

A sealant composition was compounded as follows:
Base Composition:

| Composition | Parts by Weight |
| --- | --- |
| Prepolymer of Example 3 | 100 |
| Methylon ® 75108 | 1.5 |
| T-3920* | 1.0 |
| Titanium dioxide | 1.0 |
| Silica | 1.5 |
| Hydrated Alumina | 10.0 |
| Calcium Carbonate | 50 |
| Tung Oil | 1.40 |
| Tetra N-Butyl Titanate | 0.50 |
| DABCO ® 33-LV | 0.90 |
| Silquest ® A-1100 | 0.25 |

*Commercially available from PRC-Desoto International, Inc., Sylmar, CA.

Accelerator:

| Composition | Parts by Weight |
| --- | --- |
| EPON ® 828 | 45.35 |
| DEN ® 431 | 45.35 |
| Plasticizer | 24.77 |
| Calcium Carbonate | 95.61 |
| Carbon Black | 0.46 |
| T-1601** | 0.81 |

**Commercially available from PRC-Desoto International, Inc., Sylmar, CA.

Each of the components of the Base Composition was mixed sequentially in the order listed. In a separate container, each of the components of the Accelerator was mixed sequentially in the order listed. A sealant formulation according to the present invention was prepared by mixing 100 grams of the Base Composition with 15.67 grams of the Accelerator. The sealant was cured at ambient temperature and humidity. Tensile strength and elongation were evaluated according to ASTM D412. The physical properties for the cured composition are summarized in Table 1.

TABLE 1

Physical Properties of Examples

| | Tensile Strength (psi) | Elongation (%) | Tensile Strength after Immersion* (psi) | Elongation after Immersion* (%) |
| --- | --- | --- | --- | --- |
| Example 4 | 502 | 308 | 394 | 306 |

*Tensile and elongation data were obtained after the samples were immersed in Jet Reference Fuel Type I at 140° F. for 7 days.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A sulfone-containing polythioether comprising a moiety of Formula (1):

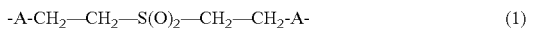

wherein
each A is independently a moiety of Formula (2):

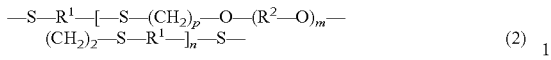

$R^1$ is —$(CH_2)_2$—O—$(CH_2)_2$—O—$(CH_2)_2$—;
p is 2;
$R^2$ is —$(CH_2)_2$—;
m is 2; and
n is an integer from 1 to 60.

2. The polythioether of claim 1, wherein the polythioether comprises a sulfone-containing polythioether adduct of Formula (3), a sulfone-containing polythioether adduct of Formula (3a), or a combination thereof:

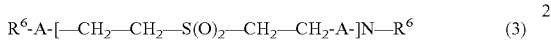

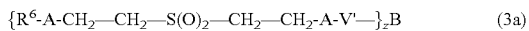

wherein
N is an integer from 1 to 10;
B represents a core of a z-valent, alkenyl-terminated polyfunctionalizing agent B(—V)$_z$ wherein:
z is an integer from 3 to 6;
each —V is a group comprising a terminal alkenyl group; and
each —V'— is derived from the reaction of —V with a thiol; and
each $R^6$ independently comprises hydrogen or a moiety having a terminal reactive group.

3. The polythioether of claim 2, wherein,
B(—V)$_z$ comprises triallyl cyanurate, which has the structure:

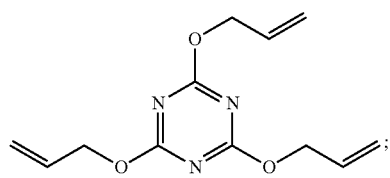 [SMILES: C=CCOc1nc(OCC=C)nc(OCC=C)n1]

z is 3;
each —V is —O—$CH_2$—CH=$CH_2$;
each —V'— is —O—$(CH_2)_3$—; and
B has the structure:

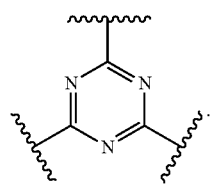 [SMILES: *c1nc(*)nc(*)n1]

4. The polythioether of claim 2, wherein each $R^6$ is hydrogen.

5. The polythioether of claim 2, wherein each $R^6$ is the same and the reactive group comprises —SH, —CH=$CH_2$, —$NH_2$, —OH, an epoxy group, a trialkylsilane group, a silyl group, —N=C=O, or a Michael acceptor group.

6. A composition comprising:
(a) the sulfone-containing polythioether of claim 1; and
(b) a curing agent that is reactive with terminal groups of the sulfone-containing polythioether.

7. The composition of claim 6, wherein each $R^6$ is hydrogen and the curing agent comprises a polyepoxy.

8. A composition comprising the sulfone-containing polythioether of claim 1, wherein the composition is formulated as a sealant.

9. A cured sealant prepared from the composition of claim 8.

10. A method of sealing a surface, comprising:
applying the composition of claim 8 to a surface; and
curing the composition to provide a sealed surface.

11. A thiol-terminated sulfone-containing polythioether comprising the reaction product of reactants comprising:
(a) a thiol-terminated polythioether adduct comprising a thiol-terminated polythioether of Formula (4), a thiol-terminated polythioether of Formula (4a), or a combination thereof:

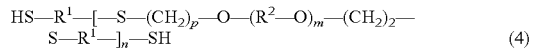

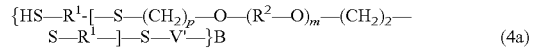

wherein,
$R^1$ is —$(CH_2)_2$—O—$(CH_2)_2$—O—$(CH_2)_2$—;
p is 2;
$R^2$ is —$(CH_2)_2$—;
m is 2;
n is an integer from 1 to 60; and
B(—V)$_z$ wherein:
z is an integer from 3 to 6;
each —V is a group comprising a terminal alkenyl group; and
each —V'— is derived from the reaction of —V with a thiol; and
(b) a sulfone of Formula (5):

12. The thiol-terminated sulfone-containing polythioether of claim 11, wherein,
B(—V)$_z$ comprises triallyl cyanurate, which has the structure:

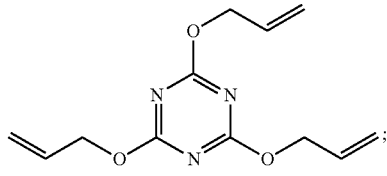 [SMILES: C=CCOc1nc(OCC=C)nc(OCC=C)n1]

z is 3;
each —V is —O—$CH_2$—CH=$CH_2$;
each —V'— is —O—$(CH_2)_3$—; and
B has the structure:

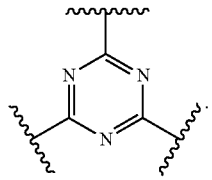

13. The polythioether of claim 11, wherein,
the adduct of Formula (4) comprises the reaction product of 1,8-dimercapto-3,6-dioxaoctane and diethylene glycol divinyl ether; and the adduct of Formula (4a) comprises the reaction product of 1,8-dimercapto-3,6-dioxaoctane, diethylene glycol divinyl ether, and triallyl cyanurate.

14. The thiol-terminated sulfone-containing polythioether of claim 11, wherein,
B(—V)$_z$ comprises triallyl cyanurate, which has the structure:

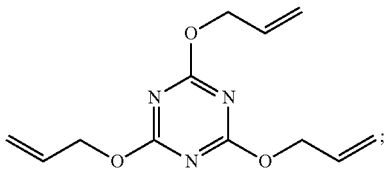 [SMILES: C=CCOc1nc(OCC=C)nc(OCC=C)n1]

z is 3;
each —V is —O—CH$_2$—CH=CH$_2$;
each —V'— is —O—(CH$_2$)$_3$—; and
B has the structure:

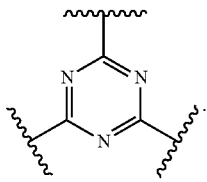 [SMILES: *c1nc(*)nc(*)n1]

15. A thiol-terminated sulfone-containing polythioether prepolymer comprising the reaction product of reactants comprising:
(a) a thiol-terminated sulfone-containing polythioether adduct comprising a thiol-terminated sulfone-containing polythioether adduct of Formula (6), a thiol-terminated sulfone-containing polythioether adduct of Formula (6a), or a combination thereof:

H-A-[—CH$_2$—CH$_2$—S(O)$_2$—CH$_2$—CH$_2$-A-]$_N$—H      (6)

{H-A-CH$_2$—CH$_2$—S(O)$_2$—CH$_2$—CH$_2$-A-V'—}$_z$B      (6a)

wherein,
N is an integer from 1 to 10;
each A is independently a moiety of Formula (2):

—S—R$^1$—[—S—(CH$_2$)$_p$—O—(R$^2$—O)$_m$—(CH$_2$)$_2$—S—R$^1$—]$_n$—S—      (2)

wherein,
R$^1$ is —(CH$_2$)$_2$—O—(CH$_2$)$_2$—O—(CH$_2$)$_2$—;
p is 2;
R$^2$ is —(CH$_2$)$_2$—;
m is 2;
n is an integer from 1 to 60; and
B represents a core of a z-valent, alkenyl-terminated polyfunctionalizing agent B(—V)$_z$, wherein,
z is an integer from 3 to 6;
each —V is a group comprising a terminal alkenyl group; and
each —V'— is derived from the reaction of —V with a thiol; and
(b) a polyalkenyl compound.

16. The prepolymer of claim 15, wherein the adduct is the adduct of Formula (6), and the polyalkenyl compound comprises diethylene glycol divinyl ether and triallyl cyanurate.

17. A composition comprising:
(a) the thiol-terminated sulfone-containing polythioether of claim 15; and
(b) a curing agent that is reactive with the terminal thiol groups of the thiol-terminated sulfone-containing polythioether.

18. A method of preparing a thiol-terminated sulfone-containing polythioether adduct of Formula (6), comprising reacting (N+1) moles of a thiol-terminated polythioether of Formula (4) with (N) moles of a sulfone of Formula (5):

H-A-[—CH$_2$—CH$_2$—S(O)$_2$—CH$_2$—CH$_2$-A-]$_N$—H      (6)

HS—R$^1$—[—S—(CH$_2$)$_p$—O—(R$^2$—O)$_m$—(CH$_2$)$_2$—S—R$^1$—]$_n$—SH      (4)

CH$_2$=CH—S(O)$_2$—CH=CH$_2$      (5)

wherein:
N is an integer from 1 to 10;
each A is independently a moiety of Formula (2):

—S—R$^1$—[—S—(CH$_2$)$_p$—O—(R$^2$—O)$_m$—(CH$_2$)$_2$—S—R$^1$—]$_n$—S—      (2)

wherein:
R$^1$ is —(CH$_2$)$_2$—O—(CH$_2$)$_2$—O—(CH$_2$)$_2$—;
p is 2;
R$^2$ is —(CH$_2$)$_2$—;
m is 2; and
n is an integer from 1 to 60.

19. A method of preparing a thiol-terminated sulfone-containing polythioether adduct of Formula (6a) comprising reacting a thiol-terminated sulfone-containing polythioether of Formula (6) with a polyfunctionalizing agent of Formula (7):

{H-A-CH$_2$—CH$_2$—S(O)$_2$—CH$_2$—CH$_2$-A-V'—}$_z$B      (6a)

H-A-CH$_2$—CH$_2$—S(O)$_2$—CH$_2$—CH$_2$-A-H      (6)

B{—V}$_z$      (7)

wherein:
each A is independently a moiety of Formula (2):

—S—R$^1$—[—S—(CH$_2$)$_p$—O—(R$^2$—O)$_m$—(CH$_2$)$_2$—S—R$^1$—]$_n$—S—      (2)

wherein:
R$^1$ is —(CH$_2$)$_2$—O—(CH$_2$)$_2$—O—(CH$_2$)$_2$—;
p is 2;
R$^2$ is —(CH$_2$)$_2$—;
m is 2; and
n is an integer from 1 to 60; and
B represents a core of a z-valent, alkenyl-terminated polyfunctionalizing agent B(—V)$_z$ wherein:
z is an integer from 3 to 6;
each —V is a group comprising a terminal alkenyl group; and
each —V'— is derived from the reaction of —V with a thiol.

20. The method of claim 19, wherein,
B(—V)$_z$ comprises triallyl cyanurate, which has the structure:

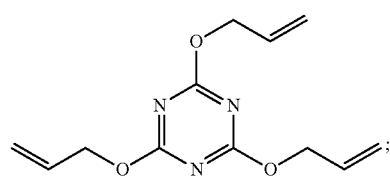 [SMILES: C=CCOc1nc(OCC=C)nc(OCC=C)n1]

z is 3;
each —V is —O—CH$_2$—CH=CH$_2$;
each —V'— is —O—(CH$_2$)$_3$—; and
B has the structure:
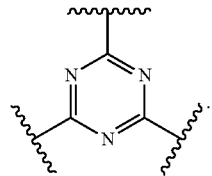
* * * * *